(12) United States Patent
Kang et al.

(10) Patent No.: US 9,523,097 B2
(45) Date of Patent: Dec. 20, 2016

(54) ENGINEERING RUBBER PRODUCTION IN PLANTS

(71) Applicant: The United States of America, as represented by the Secretary of Agriculture, Washington, DC (US)

(72) Inventors: Byung-Guk Kang, Albany, CA (US); Colleen M McMahan, Sausalito, CA (US); Maureen C Whalen, El Cerrito, CA (US); Niu Dong, San Pablo, CA (US); Shashi Kumar, New Delhi (IN)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 140 days.

(21) Appl. No.: 14/209,255

(22) Filed: Mar. 13, 2014

(65) Prior Publication Data

US 2014/0325699 A1    Oct. 30, 2014

Related U.S. Application Data

(60) Provisional application No. 61/789,228, filed on Mar. 15, 2013.

(51) Int. Cl.
*C12N 15/82* (2006.01)
*C12N 15/29* (2006.01)

(52) U.S. Cl.
CPC ....... *C12N 15/8257* (2013.01); *C12N 15/8207* (2013.01); *C12N 15/8213* (2013.01); *C12N 15/8243* (2013.01)

(58) Field of Classification Search
None
See application file for complete search history.

(56) References Cited

U.S. PATENT DOCUMENTS

| | | | |
|---|---|---|---|
| 6,541,682 B1 * | 4/2003 | Nehra | C12N 15/8216 435/417 |
| 7,129,392 B2 | 10/2006 | Hahn et al. | |
| 2003/0033626 A1 * | 2/2003 | Hahn | C12N 9/90 800/278 |
| 2003/0119098 A1 * | 6/2003 | Hallahan | C12P 9/00 435/69.1 |
| 2003/0236208 A1 * | 12/2003 | Kmiec | C12N 15/102 514/44 R |
| 2006/0217512 A1 * | 9/2006 | Mau | C12N 9/1085 528/1 |
| 2006/0248608 A1 | 11/2006 | Lelivelt et al. | |
| 2010/0218277 A1 | 8/2010 | Lelivelt et al. | |

FOREIGN PATENT DOCUMENTS

WO    WO2013036100 A1    3/2013

OTHER PUBLICATIONS

Lange et al. (PNAS, Nov. 21, 2000, vol. 97, No. 24 13172-13177).*
Payghamzadeh et al. (African Journal of Biotechnology vol. 10(3), pp. 290-311, Jan. 17, 2011).*
Kumar et al. (2012 Metab Eng. Jan. 2012; 14(1): 19-28).*
Bogorad, Lawrence, "Engineering chloroplasts: an alternative site for foreign genes, proteins, reactions and products", (2000) Tibtech, 18:257-263.
Golds, Timothy, Pal Maliga and Hans-Ulrich Koop, "Stable Plastid Transformation in PEG-treated Protoplasts of Nicotiana tabacum" (1993) Bio/Technology, 11:95-97.
Kofer, Waltraud et al., "PEG-Mediated Plastid Transformation in Higher Plants", (1998) In Vitro Cellular and Developmental Biology—Plant, (1998) 34:303-309.
Kumar, Shashi and Henry Daniell, "Engineering the Chloroplast Genome for Hyperexpression of Human Therapeutic Proteins and Vaccine Antigens" (2004) Methods in Molecular Biology, 267:365-383.
Kumar, Shashi et al., "Comparative analysis of the complete sequence of the plastid genome of *Parthenium argentatum* and identification of DNA barcodes to differentiate *Parthenium* species and lines" (2009) BMC Plant Biology, 9:131.
Kumar, Shashi et al., "Remodeling the isoprenoid pathway in tobacco by expressing the cytoplasmic mevalonate pathway in chloroplasts", (2012) Metabolic Engineering, 14:19-28.
Liu, Cheng-Wei et al., "Stable chloroplast transformation in cabbage (*Brassica oleracea* L. var. *capitata* L.) by particle bombardment", (2007) Plant Cell Reports, 26:1733-1744.
Maliga, Pal, "Plastid Transformation in Higher Plants" (2004) Annual Review of Plant Biology, 55:289-313.
Pan, Z.G. et al., "Plant regeneration from mesophyll protoplasts of Echinacea purpurea", (2004) Plant Cell, Tissue and Organ Culture, 77:251-255.
Sikdar, Sujit K., Marko Kreft and Robert Zorec, "Modulation of the unitary exocytic event amplitude by cAMP in rat melanotrophs", (1998) Journal of Physiology, 511.3:851-859.
Svab, Zora, Peter Hajdukiewicz and Pal Maliga, "Stable transformation of plastids in higher plants", (1990) Proceedings from the National Academy of Science, 87:8526-8530.
Verma, Dheeraj and Henry Daniell, "Chloroplast Vector Systems for Biotechnology Applications", (2007) Plant Physiology, 145:1129-1143.
Wu, Shuiqin et al., "Redirection of cytosolic or plastidic isoprenoid precursors elevates terpene production in plants", (2006) Nature Biotechnology, vol. 24(11):1441-1447.

* cited by examiner

*Primary Examiner* — Elizabeth McElwain
*Assistant Examiner* — Charles Logsdon
(74) *Attorney, Agent, or Firm* — David L. Marks; John D. Fado

(57) ABSTRACT

The present invention relates to transplastomic guayule plants comprising chloroplasts engineered to express the complete cytosolic mevalonic acid (MEV) pathway.

5 Claims, 9 Drawing Sheets

SEQUENCE LISTING

<160> NUMBER OF SEQ ID NOS: 12

<210> SEQ ID NO 1
<211> LENGTH: 16075
<212> TYPE: DNA
<213> ORGANISM: Artificial Sequence
<220> FEATURE:
<223> OTHER INFORMATION: DNA sequence for the guayule-specific construct
    pUY-Gua-MEV6
<220> FEATURE:
<221> NAME/KEY: source
<222> LOCATION: (1)..(1873)
<223> OTHER INFORMATION: ampicillin resistance gene in pUC19
<220> FEATURE:
<221> NAME/KEY: gene
<222> LOCATION: (1874)..(3821)
<223> OTHER INFORMATION: guayule-specific flanking sequence
<220> FEATURE:
<221> NAME/KEY: promoter
<222> LOCATION: (3823)..(3973)
<223> OTHER INFORMATION: rrn16 promoter promoter for
    spectinomycin-resistance gene
<220> FEATURE:
<221> NAME/KEY: gene
<222> LOCATION: (3993)..(4784)
<223> OTHER INFORMATION: spectinomycin-resistance gene
<220> FEATURE:
<221> NAME/KEY: gene
<222> LOCATION: (4832)..(6203)
<223> OTHER INFORMATION: =Scer PMK Phosphomevalonate
<220> FEATURE:
<221> NAME/KEY: gene
<222> LOCATION: (6203)..(7546)
<223> OTHER INFORMATION: =Scer MVKMevalonate Kinase
<220> FEATURE:
<221> NAME/KEY: gene
<222> LOCATION: (7546)..(8745)
<223> OTHER INFORMATION: =Scer MDD mevalonate diphosphate
<220> FEATURE:
<221> NAME/KEY: gene
<222> LOCATION: (8775)..(9971)
<223> OTHER INFORMATION: =Scer AAct acetoacetyl coA thiolase
<220> FEATURE:
<221> NAME/KEY: gene
<222> LOCATION: (9987)..(11462)
<223> OTHER INFORMATION: =Scer HMGS HMGCoA synthase gene
<220> FEATURE:
<221> NAME/KEY: gene
<222> LOCATION: (11487)..(12995)
<223> OTHER INFORMATION: =Scer HMGRt HMGCoA reductase
<220> FEATURE:
<221> NAME/KEY: gene
<222> LOCATION: (13025)..(13819)
<223> OTHER INFORMATION: kanamicyn resistance gene
<220> FEATURE:
<221> NAME/KEY: gene
<222> LOCATION: (13835)..(14554)
<223> OTHER INFORMATION: GFP gene
<220> FEATURE:
<221> NAME/KEY: gene
<222> LOCATION: (14576)..(14767)
<223> OTHER INFORMATION: Terminator for GFP gene

<400> SEQUENCE: 1
ctgcattaat gaatcggcca acgcgcgggg agaggcggtt tgcgtattgg gcgctcttcc     60
gcttcctcgc tcactgactc gctgcgctcg gtcgttcggc tgcggcgagc ggtatcagct    120
cactcaaagg cggtaatacg gttatccaca gaatcagggg ataacgcagg aaagaacatg    180
tgagcaaaag gccagcaaaa ggccaggaac cgtaaaaagg ccgcgttgct ggcgtttttc    240
cataggctcc gcccccctga cgagcatcac aaaaatcgac gctcaagtca gaggtggcga    300
aacccgacag gactataaag ataccaggcg tttccccctg gaagctccct cgtgcgctct    360
cctgttccga cctgccgct taccggatac ctgtccgcct ttctcccttc gggaagcgtg    420

```
gcgctttctc aatgctcacg ctgtaggtat ctcagttcgg tgtaggtcgt tcgctccaag     480
ctgggctgtg tgcacgaacc ccccgttcag cccgaccgct gcgccttatc cggtaactat     540
cgtcttgagt ccaacccggt aagacacgac ttatcgccac tggcagcagc cactggtaac     600
aggattagca gagcgaggta tgtaggcggt gctacagagt tcttgaagtg gtggcctaac     660
tacggctaca ctagaaggac agtatttggt atctgcgctc tgctgaagcc agttaccttc     720
ggaaaaagag ttggtagctc ttgatccggc aaacaaacca ccgctggtag cggtggtttt     780
tttgtttgca agcagcagat tacgcgcaga aaaaaggat ctcaagaaga tcctttgatc     840
ttttctacgg ggtctgacgc tcagtggaac gaaaactcac gttaagggat tttggtcatg     900
agattatcaa aaaggatctt cacctagatc cttttaaatt aaaaatgaag ttttaaatca     960
atctaaagta tatatgagta aacttggtct gacagttacc aatgcttaat cagtgaggca    1020
cctatctcag cgatctgtct atttcgttca tccatagttg cctgactccc cgtcgtgtag    1080
ataactacga tacgggaggg cttaccatct ggccccagtg ctgcaatgat accgcgagac    1140
ccacgctcac cggctccaga tttatcagca ataaccagc cagccggaag ggccgagcgc    1200
agaagtggtc ctgcaacttt atccgcctcc atccagtcta ttaattgttg ccgggaagct    1260
agagtaagta gttcgccagt taatagtttg cgcaacgttg ttgccattgc tacaggcatc    1320
gtggtgtcac gctcgtcgtt tggtatggct tcattcagct ccggttccca acgatcaagg    1380
cgagttacat gatcccccat gttgtgcaaa aaagcggtta gctccttcgg tcctccgatc    1440
gttgtcagaa gtaagttggc cgcagtgtta tcactcatgg ttatggcagc actgcataat    1500
tctcttactg tcatgccatc cgtaagatgc ttttctgtga ctggtgagta ctcaaccaag    1560
tcattctgag aatagtgtat gcggcgaccg agttgctctt gcccggcgtc aatacgggat    1620
aataccgcgc cacatagcag aactttaaaa gtgctcatca ttggaaaacg ttcttcgggg    1680
cgaaaactct caaggatctt accgctgttg agatccagtt cgatgtaacc cactcgtgca    1740
cccaactgat cttcagcatc ttttactttc accagcgttt ctgggtgagc aaaaacagga    1800
aggcaaaatg ccgcaaaaaa gggaataagg gcgacacgga aatgttgaat actcatactc    1860
ttcctttttc aatggccgac actgacactg agagacgaaa gctaggggag cgaatgggat    1920
tagatacccc agtagtccta gccgtaaacg atggatacta ggcgctgtgc gtatcgaccc    1980
gtgcagtgct gtagctaacg cgttaagtat cccgcctggg gagtacgttc gcaagaatga    2040
aactcaaagg aattgacggg ggcccgcaca agcggtggag catgtggttt aattcgatgc    2100
aaagcgaaga accttaccag ggcttgacat gccgcgaatc ctcttgaaag agagggtgc    2160 cttcgggaac gcggacacag gtggtgcatg gctgtcgtca gctcgtgccg taaggtgttg    2220
ggttaagtcc cgcaacgagc gcaaccctcg tgtttagttg ccatcattga gtttggaacc    2280
ctgaacagac tgccggtgat aagccggagg aaggtgagga tgacgtcaag tcatcatgcc    2340
ccttatgccc tggcgacac acgtgctaca atggccggga caaagggtcg cgatcccgcg    2400
agggtgagct aactccaaaa acccgtcctc agttcggatt gcaggctgca actcgcctgc    2460
atgaagccgg aatcgctagt aatcgccggt cagccatacg gcggtgaatc cgttcccggg    2520
ccttgtacac accgcccgtc acactatggg agctggccat gcccgaagtc gttaccttaa    2580
ccgcaaggag ggggatgccg aaggcagggc tagtgactgg agtgaagtcg taacaaggta    2640
gccgtactgg aaggtgcggc tggatcacct ccttttcagg gagagctaat gcttgttggg    2700
tattttggtt taacactgct tcacacccaa aaagaaggga gctacgtctg agtgaaactt    2760
```

-continued

| | |
|---|---|
| ggagatggaa gtcttctttc gtttctcgac agtgaagtaa gaccaagctc atgagcttat | 2820 |
| tatctcaggt cggaacaagt tgataggatc cccctttttta cgtccccatg ccgcctgtgt | 2880 |
| ggtgacatgg gccgaaaaaa ggaaagagag ggatggggtt tctctcgctt ttggcatagt | 2940 |
| gggcccccgg tgggggctc gcacgacggg ctattagctc agtggtagag cgcgccctg | 3000 |
| ataattgcgt cgttgtgcct gggctgtgag ggctctcagc cacatggata gttcaatgtg | 3060 |
| ctcatcggcg cctgaccctg agatgtggat catccaaggc acattagcat ggcgtactcc | 3120 |
| tcctgttcga accggggttt gaaaccaaac ttctcctcag gaggatagat ggggcgattc | 3180 |
| aggtgagatc caatgtagat ccaactttcg attcactcgt gggatccggg cggtccgggg | 3240 |
| gggaccacca tggctcctct cttctcgaga atccatacat cccttatcag tgtatggaca | 3300 |
| gctatctctc gagcacaggt ttaggttcgg cctcaatggg aaaataaaat ggagcaccta | 3360 |
| acaacgcatc ttcacagacc aagaactacg agatcacccc tttcattctg gggtgacgga | 3420 |
| gggatcatac cattcgagcc ttttttttc atgcttttcc ccgaggtctg gagaaagctg | 3480 |
| aaatcaaatg ggatgtgtct atttatctat ctcttgactc gaaatgggag caggtttgaa | 3540 |
| aaaggatctt agagtgtcta gggttgggcc aggagggtct cttaacgcct tcttttttct | 3600 |
| tctcatcgga gttctttcac aaagacttgc catggtaagg aagaaggggg aacaggcac | 3660 |
| acttggagag cgcagtacaa cggagagttg tatgctgcgt tcgggaagga tgaatcgctc | 3720 |
| ccgagaaagg aatctattga ttctctccca attggttgga ccgtaggtgc gatgatttac | 3780 |
| ttcacgggcg aggtctctgg ttcaagtcca ggatggccca gggccgcaat gtgagttttt | 3840 |
| gtagttggat ttgctccccc gccgtcgttc aatgagaatg gataagaggc tcgtgggatt | 3900 |
| gacgtgaggg ggcagggatg gctatatttc tgggagcgaa ctccgggcga atatgaagcg | 3960 |
| catcgataca agtgagttgt agggagggaa ccatggcaga agcggtgatc gccgaagtat | 4020 |
| cgactcaact atcagaggta gttggcgtca tcgagcgcca tctcgaaccg acgttgctgg | 4080 |
| ccgtacattt gtacggctcc gcagtggatg gcggcctgaa gccacacagt gatattgatt | 4140 |
| tgctggttac ggtgaccgta aggcttgatg aaacaacgcg gcgagctttg atcaacgacc | 4200 |
| ttttggaaac ttcggcttcc cctggagaga gcgagattct ccgcgctgta gaagtcacca | 4260 |
| ttgttgtgca cgacgacatc attccgtggc gttatccagc taagcgcgaa ctgcaatttg | 4320 |
| gagaatggca gcgcaatgac attcttgcag gtatcttcga ccagccacg atcgacattg | 4380 |
| atctggctat cttgctgaca aaagcaagag aacatagcgt tgccttggta ggtccagcgg | 4440 |
| cggaggaact ctttgatccg gttcctgaac aggatctatt tgaggcgcta atgaaacct | 4500 |
| taacgctatg gaactcgccg cccgactggg ctggcgatga gcgaaatgta gtgcttacgt | 4560 |
| tgtcccgcat ttggtacagc gcagtaaccg gcaaaatcgc gccgaaggat gtcgctgccg | 4620 |
| actgggcaat ggagcgcctg ccggcccagt atcagcccgt catacttgaa gctagacagg | 4680 |
| cttatcttgg acaagaagaa gatcgcttgg cctcgcgcgc agatcagttg gaagaatttg | 4740 |
| tccactacgt gaaaggcgag atcaccaagg tagtcggcaa ataaatctaa gccgaattct | 4800 |
| gcagatccta ggggccgcag gaggagttca tatgtcagag ttgagagcct tcagtgcccc | 4860 |
| agggaaagcg ttactagctg gtggatattt agttttagat acaaaatatg aagcatttgt | 4920 |
| agtcggatta tcggcaagaa tgcatgctgt agcccatcct tacggttcat tgcaagggtc | 4980 |
| tgataagttt gaagtgcgtg tgaaaagtaa acaatttaaa gatggggagt ggctgtacca | 5040 |
| tataagtcct aaaagtggct tcattcctgt ttcgataggc ggatctaaga acccttttcat | 5100 |
| tgaaaaagtt atcgctaacg tatttagcta cttaaacct aacatggacg actactgcaa | 5160 |

```
tagaaacttg ttcgttattg atattttctc tgatgatgcc taccattctc aggaggatag    5220
cgttaccgaa catcgtggca acagaagatt gagtttcat tcgcacagaa ttgaagaagt    5280
tcccaaaaca gggctgggct cctcggcagg tttagtcaca gttttaacta cagctttggc    5340 ctccttttt gtatcggacc tggaaaataa tgtagacaaa tatagagaag ttattcataa    5400
tttagcacaa gttgctcatt gtcaagctca gggtaaaatt ggaagcgggt tgatgtagc    5460 ggcggcagca tatggatcta tcagatatag aagattccca cccgcattaa tctctaattt    5520
gccagatatt ggaagtgcta cttacggcag taaactggcg catttggttg atgaagaaga    5580
ctggaatatt acgattaaaa gtaaccattt accttcggga ttaactttat ggatgggcga    5640
tattaagaat ggttcagaaa cagtaaaact ggtccagaag gtaaaaaatt ggtatgattc    5700
gcatatgcca gaaagcttga aaatatatac agaactcgat catgcaaatt ctagatttat    5760
ggatggacta tctaaactag atcgcttaca cgagactcat gacgattaca gcgatcagat    5820
atttgagtct cttgagagga atgactgtac ctgtcaaaag tatcctgaaa tcacagaagt    5880
tagagatgca gttgccacaa ttagacgttc ctttagaaaa ataactaaag aatctggtgc    5940
cgatatcgaa cctcccgtac aaactagctt attggatgat tgccagacct taaaaggagt    6000
tcttacttgc ttaatacctg gtgctggtgg ttatgacgcc attgcagtga ttactaagca    6060
agatgttgat cttagggctc aaaccgctaa tgacaaaaga ttttctaagg ttcaatggct    6120
ggatgtaact caggctgact ggggtgttag gaaagaaaaa gatccggaaa ctttatcttg    6180
ataaactgca ggaggagttt taatgtcatt accgttctta acttctgcac cgggaaaggt    6240
tattattttt ggtgaacact ctgctgtgta caacaagcct gccgtcgctg ctagtgtgtc    6300
tgcgttgaga acctacctgc taataagcga gtcatctgca ccagatacta ttgaattgga    6360
cttcccggac attagcttta atcataagtg gtccatcaat gatttcaatg ccatcaccga    6420
ggatcaagta aactcccaaa aattggccaa ggctcaacaa gccaccgatg gcttgtctca    6480
ggaactcgtt agtctttgg atccgttgtt agctcaacta tccgaatcct tccactacca    6540
tgcagcgttt tgtttcctgt atatgtttgt ttgcctatgc ccccatgcca agaatattaa    6600
gttttcttta aagtctactt tacccatcgg tgctgggttg ggctcaagcg cctctatttc    6660
tgtatcactg gccttagcta tggcctactt gggggggtta ataggatcta atgacttgga    6720
aaagctgtca gaaacgata agcatatagt gaatcaatgg gccttcatag gtgaaaagtg    6780
tattcacggt accccttcag gaatagataa cgctgtggcc acttatggta atgccctgct    6840
atttgaaaaa gactcacata atggaacaat aaacacaaac aatttaagt tcttagatga    6900 tttcccagcc attccaatga tcctaaccta tactagaatt ccaaggtcta caaaagatct    6960
tgttgctcgc gttcgtgtgt tggtcaccga gaaattcct gaagttatga agccaattct    7020
agatgccatg ggtgaatgtg ccctacaagg cttagagatc atgactaagt taagtaaatg    7080
taaaggcacc gatgacgagg ctgtagaaac taataatgaa ctgtatgaac aactattgga    7140
attgataaga ataaatcatg gactgcttgt ctcaatcggt gtttctcatc ctggattaga    7200
acttattaaa aatctgagcg atgatttgag aattggctcc acaaaactta ccggtgctgg    7260
tggcggcggt tgctctttga ctttgttacg aagagacatt actcaagagc aaattgacag    7320
cttcaaaaag aaattgcaag atgattttag ttacgagaca tttgaaacag acttgggtgg    7380
gactggctgc tgtttgttaa gcgcaaaaaa tttgaataaa gatcttaaaa tcaaatccct    7440
agtattccaa ttatttgaaa ataaaactac cacaaagcaa caaattgacg atctattatt    7500
```

```
gccaggaaac acgaatttac catggacttc acaggaggag ttttaatgac tgtatatact    7560
gctagtgtaa ctgctccggt aaatattgct actcttaagt attggggaa aagggacacg     7620
aagttgaatc tgcccaccaa ttcgtccata tcagtgactt tatcgcaaga tgacctcaga    7680
acgttgacct ctgcggctac tgcacctgag tttgaacgcg acactttgtg gttaaatgga    7740
gaaccacaca gcatcgacaa tgaaagaact caaaattgtc tgcgcgacct acgccaatta   7800
agaaaggaaa tggaatcgaa ggacgcctca ttgcccacat tatctcaatg gaaactccac   7860
attgtctccg aaaataactt tcctacagca gctggtttag cttcctccgc tgctggcttt   7920
gctgcattgg tctctgcaat tgctaagtta taccaattac cacagtcaac ttcagaaata   7980
tctagaatag caagaaaggg gtctggttca gcttgtagat cgttgtttgg cggatacgtg   8040
gcctgggaaa tgggaaaagc tgaagatggt catgattcca tggcagtaca atcgcagac    8100
agctctgact ggcctcagat gaaagcttgt gtcctagttg tcagcgatat taaaaaggat   8160
gtgagttcca ctcagggtat gcaattgacc gtggcaacct ccgaactatt taaagaaaga   8220
attgaacatg tcgtaccaaa gagatttgaa gtcatgcgta aagccattgt tgaaaaagat   8280
ttcgccacct ttgcaaagga acaatgatg gattccaact cttcccatgc cacatgtttg    8340
gactcttttcc ctccaatatt ctacatgaat gacacttcca agcgtatcat cagttggtgc   8400
cacaccatta atcagtttta cggagaaaca atcgttgcat acacgtttga tgcaggtcca   8460
aatgctgtgt tgtactactt agctgaaaat gagtcgaaac tctttgcatt tatctataaa   8520
ttgtttggct ctgttcctgg atgggacaag aaatttacta ctgagcagct tgaggctttc   8580
aaccatcaat ttgaatcatc taactttact gcacgtgaat tggatcttga gttgcaaaag   8640
gatgttgcca gagtgatttt aactcaagtc ggttcaggcc cacaagaaac aaacgaatct   8700
ttgattgacg caaagactgg tctaccaaag gaagaggagt tttaactcga gggggggccc   8760
taggaggtat aacaatgtct cagaacgttt acattgtatc gactgccaga accccaattg   8820
gttcattcca gggttctcta tcctccaaga cagcagtgga attgggtgct gttgctttaa   8880
aaggcgcctt ggctaaggtt ccagaattgg atgcatccaa ggattttgac gaaattattt   8940
ttggtaacgt tctttctgcc aatttgggcc aagctccggc cagacaagtt gctttggctg   9000
ccggtttgag taatcatatc gttgcaagca cagttaacaa ggtctgtgca tccgctatga   9060
aggcaatcat tttgggtgct caatccatca aatgtggtaa tgctgatgtt gtcgtagctg   9120
gtggttgtga atctatgact aacgcaccat actacatgcc agcagcccgt gcgggtgcca   9180
aatttggcca aactgttctt gttgatggtg tcgaaagaga tgggttgaac gatgcgtacg   9240
atggtctagc catgggtgta cacgcagaaa agtgtgcccg tgattgggat attactagag   9300
aacaacaaga caattttgcc atcgaatcct accaaaaatc tcaaaaatct caaaaggaag   9360
gtaaattcga caatgaaatt gtacctgtta ccattaaggg atttagaggt aagcctgata   9420
ctcaagtcac gaaggacgag gaacctgcta gattacacgt tgaaaaattg agatctgcaa   9480
ggactgtttt ccaaaaagaa aacggtactg ttactgccgc taacgcttct ccaatcaacg   9540
atggtgctgc agccgtcatc ttggtttccg aaaaagtttt gaaggaaaag aatttgaagc   9600
ctttggctat tatcaaaggt tggggtgagg ccgctcatca accagctgat tttacatggg   9660
ctccatctct tgcagttcca aaggctttga acatgctggg catcgaagac atcaattctg   9720
ttgattactt tgaattcaat gaagcctttt cggttgtcgg tttggtgaac actaagattt   9780
tgaagctaga cccatctaag gttaatgtat atggtggtgc tgttgctcta ggtcacccat   9840
tgggttgttc tggtgctaga gtggttgtta cactgctatc catcttacag caagaaggag   9900
```

```
gtaagatcgg tgttgccgcc atttgtaatg gtggtggtgg tgcttcctct attgtcattg   9960
aaaagatatg aacaggaggt ataacaatga aactctcaac taaactttgt tggtgtggta  10020
ttaaaggaag acttaggccg caaaagcaac aacaattaca caatacaaac ttgcaaatga  10080
ctgaactaaa aaaacaaaag accgctgaac aaaaaaccag acctcaaaat gtcggtatta  10140
aaggtatcca aatttacatc ccaactcaat gtgtcaacca atctgagcta gagaaatttg  10200
atggcgtttc tcaaggtaaa tacacaattg gtctgggcca aaccaacatg tcttttgtca  10260
atgacagaga agatatctac tcgatgtccc taactgtttt gtctaagttg atcaagagtt  10320
acaacatcga caccaacaaa attggtagat tagaagtcgg tactgaaact ctgattgaca  10380
agtccaagtc tgtcaagtct gtcttgatgc aattgtttgg tgaaaacact gacgtcgaag  10440
gtattgacac gcttaatgcc tgttacggtg gtaccaacgc gttgttcaac tctttgaact  10500
ggattgaatc taacgcatgg gatggtagag acgccattgt agtttgcggt gatattgcca  10560
tctacgataa gggtgccgca agaccaaccg gtggtgccgg tactgttgct atgtggatcg  10620
gtcctgatgc tccaattgta tttgactctg taagagcttc ttacatggaa cacgcctacg  10680 attttttacaa gccagatttc accagcgaat atccttacgt cgatggtcat ttttcattaa  10740
cttgttacgt caaggctctt gatcaagttt acaagagtta ttccaagaag gctatttcta  10800
aagggttggt tagcgatccc gctggttcgg atgctttgaa cgttttgaaa tatttcgact  10860
acaacgtttt ccatgttcca acctgtaaat tggtcacaaa atcatacggt agattactat  10920
ataacgattt cagagccaat cctcaattgt tcccagaagt tgacgccgaa ttagctactc  10980
gcgattatga cgaatcttta accgataaga acattgaaaa aacttttgtt aatgttgcta  11040
agccattcca caaagagaga gttgcccaat ctttgattgt tccaacaaac acaggtaaca  11100
tgtacaccgc atctgtttat gccgcctttg catctctatt aaactatgtt ggatctgacg  11160
acttacaagg caagcgtgtt ggtttatttt cttacggttc cggtttagct gcatctctat  11220
attcttgcaa aattgttggt gacgtccaac atattatcaa ggaattagat attactaaca  11280
aattagccaa gagaatcacc gaaactccaa aggattacga agctgccatc gaattgagag  11340
aaaatgccca tttgaagaag aacttcaaac ctcaaggttc cattgagcat ttgcaaagtg  11400
gtgtttacta cttgaccaac atcgatgaca aatttagaag atcttacgat gttaaaaaat  11460
aacccgcccc gggaggaggt ataacaatgg ttttaaccaa taaaacagtc atttctggat  11520
cgaaagtcaa aagtttatca tctgcgcaat cgagctcatc aggaccttca tcatctagtg  11580
aggaagatga ttcccgcgat attgaaagct tggataagaa aatacgtcct ttagaagaat  11640
tagaagcatt attaagtagt ggaaatacaa acaattgaa gaacaaagag gtcgctgcct  11700
tggttattca cggtaagtta cctttgtacg ctttggagaa aaaattaggt gatactacga  11760
gagcggttgc ggtacgtagg aaggctcttt caattttggc agaagctcct gtattagcat  11820
ctgatcgttt accatataaa aattatgact acgaccgcgt atttggcgct tgttgtgaaa  11880
atgttatagg ttacatgcct ttgcccgttg gtgttatagg ccccttggtt atcgatggta  11940
catcttatca tataccaatg gcaactacag agggttgttt ggtagcttct gccatgcgtg  12000
gctgtaaggc aatcaatgct ggcggtgtg caacaactgt tttaactaag gatggtatga  12060
caagaggccc agtagtccgt ttcccaactt tgaaaagatc tggtgcctgt aagatatggt  12120
tagactcaga agagggacaa aacgcaatta aaaaagcttt taactctaca tcaagatttg  12180
cacgtctgca acatattcaa acttgtctag caggagattt actcttcatg agatttagaa  12240
```

```
caactactgg tgacgcaatg ggtatgaata tgatttctaa aggtgtcgaa tactcattaa    12300
agcaaatggt agaagagtat ggctgggaag atatggaggt tgtctccgtt tctggtaact    12360
actgtaccga caaaaaacca gctgccatca actggatcga aggtcgtggt aagagtgtcg    12420
tcgcagaagc tactattcct ggtgatgttg tcagaaaagt gttaaaaagt gatgtttccg    12480
cattggttga gttgaacatt gctaagaatt tggttggatc tgcaatggct gggtctgttg    12540
gtggatttaa cgcacatgca gctaatttag tgacagctgt tttcttggca ttaggacaag    12600
atcctgcaca aaatgttgaa agttccaact gtataacatt gatgaaagaa gtggacggtg    12660
atttgagaat ttccgtatcc atgccatcca tcgaagtagg taccatcggt ggtggtactg    12720
ttctagaacc acaaggtgcc atgttggact tattaggtgt aagaggcccg catgctaccg    12780
ctcctggtac caacgcacgt caattagcaa aatagttgc ctgtgccgtc ttggcaggtg    12840
aattatcctt atgtgctgcc ctagcagccg gccatttggt tcaaagtcat atgacccaca    12900
acaggaaacc tgctgaacca acaaaaaccta acaatttgga cgccactgat ataaatcgtt    12960
tgaaagatgg gtccgtcacc tgcattaaat cctaagttgg ccccgggcgg ccgctcgcga    13020
aggcatgatt gaacaagatg gattgcacgc aggttctccg gccgcttggg tggagaggct    13080
attcggctat gactgggcac aacagacaat cggctgctct gatgccgccg tgttccggct    13140
gtcagcgcag gggcgcccgg ttcttttgt caagaccgac ctgtccggtg ccctgaatga    13200
actgcaggac gaggcagcgc ggctatcgtg gctggccacg acgggcgttc cttgcgcagc    13260
tgtgctcgac gttgtcactg aagcgggaag ggactggctg ctattgggcg aagtgccggg    13320
gcaggatctc ctgtcatccc accttgctcc tgccgagaaa gtatccatca tggctgatgc    13380
aatgcggcgg ctgcatacgc ttgatccggc tacctgccca ttcgaccacc aagcgaaaca    13440
tcgcatcgag cgagcacgta ctcggatgga agccggtctt gtcgatcagg atgatctgga    13500
cgaagagcat caggggctcg cgccagccga actgttcgcc aggctcaagg cgcgcatgcc    13560
cgacggcgag gatctcgtcg tgacccatgg cgatgcctgc ttgccgaata tcatggtgga    13620
aaatggccgc ttttctggat tcatcgactg tggccggctg ggtgtggcgg accgctatca    13680
ggacatagcg ttggctaccc gtgatattgc tgaagagctt ggcggcgaat gggctgaccg    13740
cttcctcgtg ctttacggta tcgccgctcc cgattcgcag cgcatcgcct tctatcgcct    13800
tcttgacgag ttcttctgaa ggcctgagga gtttatggtg agcaagggcg aggagctgtt    13860
caccggggtg gtgcccatcc tggtcgagct ggacggcgac gtaaacggcc acaagttcag    13920
cgtgtccggc gagggcgagg gcgatgccac ctacggcaag ctgaccctga agttcatctg    13980
caccaccggc aagctgcccg tgccctggcc caccctcgtg accaccctga cctacggcgt    14040
gcagtgcttc agccgctacc ccgaccacat gaagcagcac gacttcttca agtccgccat    14100
gcccgaaggc tacgtccagg agcgcaccat cttcttcaag gacgacggca actacaagac    14160
ccgcgccgag gtgaagttcg agggcgacac cctggtgaac cgcatcgagc tgaagggcat    14220
cgacttcaag gaggacggca acatcctggg gcacaagctg gagtacaact acaacagcca    14280
caacgtctat atcatggccg acaagcagaa gaacggcatc aaggtgaact tcaagatccg    14340
ccacaacatc gaggacggca gcgtgcagct cgccgaccac taccagcaga acacccccat    14400
cggcgacggc cccgtgctgc tgcccgacaa ccactacctg agcacccagt ccgccctgag    14460
caaagacccc aacgagaagc gcgatcacat ggtcctgctg gagttcgtga ccgccgccgg    14520
gatcactctc ggcatggacg agctgtacaa gtaaaggcct gttccttaat ctagagcgat    14580
cctggcctag tctataggag gttttgaaaa gaaaggagca ataatcattt tcttgttcta    14640
```

-continued

```
tcaaagaggg tgctattgct cctttctttt tttcttttta tttatttact agtattttac    14700
ttacatagac ttttttgttt acattataga aaaagaagga gaggttattt tcttgcattt    14760
attcatgatt gagtattcta ttttgatttt gtatttgttt gggctgcagg tcaactgccc    14820
ctatcggaaa taggattgac taccgattcc gaaggaactg gagttacatc tcttttccat    14880
tcaagagttc ttatgcgttt ccacgcccct tgagacccc gaaaaatgga caaattcctt     14940
ttcttaggaa cacatacaag attcgtcact acaaaaagga taatggtaac ctgcgccagg    15000
gaaaagaata aagaagcat ctgactactt catgcatgct ccacttggct cgggggata      15060
tagctcagtt ggtagagctc cgctcttgca attgggtcgt tgcgattacg ggttggatgt    15120
ctaattgtcc aggcggtaat gatagtatct tgtacctgaa ccggtggctc acttttttcta   15180
agtaatgggg aagaggaccg aaacatgcca ctgaaagact ctactgagac aaagatgggc    15240
tgtcaagaac gtcaagaacg tagaggaggt aggatgggca gttggtcaga tctagtatgg    15300
atcgtacatg gacggtagtt ggagtcggcg gctctcctag ggttcccta tcggggatcc     15360
ctggggaaga ggatcaagtt ggcccttgcg aacagcttga tgcactatct cccttcaacc    15420
ctttgagcga aatacggcaa aaggaaggaa aatccatgga ccgaccccat catctccacc    15480
ccgtaggaac tacgagatta ccccaaggac gccttcggca tccaggggtc acggaccgac    15540
catagaaccc tgttcaataa gtggaacgca ttagctgtcc gctctcaggt tgggcagtaa    15600
gggtcggaga agggcaatca ctcattctta aaaccagcgt tcttaaggcc aaagagtcgg    15660
cggaaaaggg gggaaagctc tccgttcctg gttctcctgt agctggatcc tccggaacca    15720
caagaatcct tagttagaat tagaatgcga ttccaactca gcacctttg agttagattt     15780
tgagaagagt tgctctttgg agagcacagt acgatgaaag ttgtaagctg tgttcggggg    15840
ggagttattg tctatcgttg gcctctatgg tagaatcagt cggggacct gagaggcggt      15900
ggtttacct gcggcggatg tcagcggttc gagtccgctt atctccaact cgtgaactta     15960
gccgatacaa agctatatga tagcacccaa ttttccgat tcggcggttc gatctatgat      16020
ttatcattca tggacgttga taagatccat ccatttagca gcaccttagg atggc          16075
```

```
<210> SEQ ID NO 2
<211> LENGTH: 20
<212> TYPE: DNA
<213> ORGANISM: Artificial Sequence
<220> FEATURE:
<223> OTHER INFORMATION: PRIMER

<400> SEQUENCE: 2
ttggacttcc cggacattag                                                20

<210> SEQ ID NO 3
<211> LENGTH: 20
<212> TYPE: DNA
<213> ORGANISM: Artificial Sequence
<220> FEATURE:
<223> OTHER INFORMATION: PRIMER

<400> SEQUENCE: 3
tttctcggtg accaacacac                                                20

<210> SEQ ID NO 4
<211> LENGTH: 20
<212> TYPE: DNA
<213> ORGANISM: Artificial Sequence
<220> FEATURE:
```

<223> OTHER INFORMATION: PRIMER

<400> SEQUENCE: 4
tgaatgaact gcaggacgag                                           20

<210> SEQ ID NO 5
<211> LENGTH: 20
<212> TYPE: DNA
<213> ORGANISM: Artificial Sequence
<220> FEATURE:
<223> OTHER INFORMATION: PRIMER

<400> SEQUENCE: 5
gggtgttctg ctggtagtgg                                           20

<210> SEQ ID NO 6
<211> LENGTH: 20
<212> TYPE: DNA
<213> ORGANISM: Artificial Sequence
<220> FEATURE:
<223> OTHER INFORMATION: PRIMER

<400> SEQUENCE: 6
ctgaagttca tctgcaccac                                           20

<210> SEQ ID NO 7
<211> LENGTH: 20
<212> TYPE: DNA
<213> ORGANISM: Artificial Sequence
<220> FEATURE:
<223> OTHER INFORMATION: PRIMER

<400> SEQUENCE: 7
ggtgctcagg tagtggttgt                                           20

<210> SEQ ID NO 8
<211> LENGTH: 25
<212> TYPE: DNA
<213> ORGANISM: Artificial Sequence
<220> FEATURE:
<223> OTHER INFORMATION: PRIMER

<400> SEQUENCE: 8
ggccgacact gacactgaga gacga                                     25

<210> SEQ ID NO 9
<211> LENGTH: 26
<212> TYPE: DNA
<213> ORGANISM: Artificial Sequence
<220> FEATURE:
<223> OTHER INFORMATION: PRIMER

<400> SEQUENCE: 9
gccatcctaa ggtgctgcta aatgga                                    26

<210> SEQ ID NO 10
<211> LENGTH: 3033
<212> TYPE: DNA
<213> ORGANISM: Parthenium argentatum

<400> SEQUENCE: 10
ggccgacact gacactgaga gacgaaagct aggggagcga atgggattag atacccagt    60 agtcctagcc gtaaacgatg gatactaggc gctgtgcgta tcgacccgtg cagtgctgta  120
gctaacgcgt taagtatccc gcctggggag tacgttcgca agaatgaaac tcaaaggaat  180

```
tgacggggc  ccgcacaagc  ggtggagcat  gtggtttaat  tcgatgcaaa  gcgaagaacc      240
ttaccagggc  ttgacatgcc  gcgaatcctc  ttgaaagaga  ggggtgcctt  cgggaacgcg      300
gacacaggtg  gtgcatggct  gtcgtcagct  cgtgccgtaa  ggtgttgggt  taagtcccgc      360
aacgagcgca  accctcgtgt  ttagttgcca  tcattgagtt  tggaacccctg  aacagactgc     420 cggtgataag  ccggaggaag  gtgaggatga  cgtcaagtca  tcatgcccct  tatgccctgg      480
gcgacacacg  tgctacaatg  gccgggacaa  agggtcgcga  tcccgcgagg  gtgagctaac      540
tccaaaaacc  cgtcctcagt  tcggattgca  ggctgcaact  cgcctgcatg  aagccggaat      600
cgctagtaat  cgccggtcag  ccatacggcg  gtgaatccgt  tcccgggcct  tgtacacacc      660
gcccgtcaca  ctatgggagc  tggccatgcc  cgaagtcgtt  accttaaccg  caaggagggg      720
gatgccgaag  gcagggctag  tgactggagt  gaagtcgtaa  caaggtagcc  gtactggaag      780
gtgcggctgg  atcacctcct  tttcaggag  agctaatgct  tgttgggtat  tttggtttaa       840
cactgcttca  cacccaaaaa  gaagggagct  acgtctgagt  gaaacttgga  gatggaagtc      900
ttctttcgtt  tctcgacagt  gaagtaagac  caagctcatg  agcttattat  ctcaggtcgg      960
aacaagttga  taggatcccc  ctttttacgt  ccccatgccg  cctgtgtggt  gacatgggcc     1020
gaaaaaagga  aagagaggga  tggggtttct  ctcgcttttg  gcatagtggg  ccccggtgg      1080 ggggctcgca  cgacgggcta  ttagctcagt  ggtagagcgc  gcccctgata  attgcgtcgt     1140
tgtgcctggg  ctgtgagggc  tctcagccac  atggatagtt  caatgtgctc  atcggcgcct     1200
gaccctgaga  tgtggatcat  ccaaggcaca  ttagcatggc  gtactcctcc  tgttcgaacc     1260
ggggtttgaa  accaaacttc  tcctcaggag  gatagatggg  gcgattcagg  tgagatccaa     1320
tgtagatcca  actttcgatt  cactcgtggg  atccgggcgg  tccggggggg  accaccatgg     1380
ctcctctctt  ctcgagaatc  catacatccc  ttatcagtgt  atggacagct  atctctcgag     1440
cacaggttta  ggttcggcct  caatgggaaa  ataaaatgga  gcacctaaca  acgcatcttc     1500
acagaccaag  aactacgaga  tcacccctttt  cattctgggg  tgacggaggg  atcataccat    1560
tcgagccttt  tttttttcatg  cttttccccg  aggtctggag  aaagctgaaa  tcaaatggga    1620
tgtgtctatt  tatctatctc  ttgactcgaa  atgggagcag  gtttgaaaaa  ggatcttaga    1680
gtgtctaggg  ttgggccagg  agggtctctt  aacgccttct  ttttcttct   catcggagtt    1740 ctttcacaaa  gacttgccat  ggtaaggaag  aaggggggaa  caggcacact  tggagagcgc     1800
agtacaacgg  agagttgtat  gctgcgttcg  ggaaggatga  atcgctcccg  agaaaggaat     1860
ctattgattc  tctcccaatt  ggttggaccg  taggtgcgat  gatttacttc  acgggcgagg     1920
tctctggttc  aagtccagga  tggcccagct  gcgccaggga  aaagaataga  agaagcatct     1980
gactacttca  tgcatgctcc  acttggctcg  ggggatata   gctcagttgg  tagagctccg     2040
ctcttgcaat  tgggtcgttg  cgattacggg  ttggatgtct  aattgtccag  gcggtaatga     2100
tagtatcttg  tacctgaacc  ggtggctcac  ttttttctaag  taatgggaa   gaggaccgaa    2160 acatgccact  gaaagactct  actgagacaa  agatgggctg  tcaagaacgt  caagaacgta     2220
gaggaggtag  gatgggcagt  tggtcagatc  tagtatggat  cgtacatgga  cggtagttgg     2280
agtcggcggc  tctcctaggg  ttcccttatc  ggggatccc   ggggaagagg  atcaagttgg     2340
cccttgcgaa  cagcttgatg  cactatctcc  cttcaaccct  ttgagcgaaa  tacggcaaaa     2400
ggaaggaaaa  tccatggacc  gaccccatca  tctccacccc  gtaggaacta  cgagattacc     2460
ccaaggacgc  cttcggcatc  caggggtcac  ggaccgacca  tagaaccctg  ttcaataagt     2520
```

```
ggaacgcatt agctgtccgc tctcaggttg ggcagtaagg gtcggagaag ggcaatcact    2580
cattcttaaa accagcgttc ttaaggccaa agagtcggcg gaaaaggggg gaaagctctc    2640
cgttcctggt tctcctgtag ctggatcctc cggaaccaca agaatcctta gttagaatta    2700
gaatgcgatt ccaactcagc acctttgag ttagattttg agaagagttg ctctttggag    2760
agcacagtac gatgaaagtt gtaagctgtg ttcgggggg agttattgtc tatcgttggc    2820
ctctatggta gaatcagtcg ggggacctga gaggcggtgg tttaccctgc ggcggatgtc    2880
agcggttcga gtccgcttat ctccaactcg tgaacttagc cgatacaaag ctatatgata    2940
gcacccaatt tttccgattc ggcggttcga tctatgattt atcattcatg gacgttgata    3000
agatccatcc atttagcagc accttaggat ggc                                 3033

<210> SEQ ID NO 11
<211> LENGTH: 20
<212> TYPE: DNA
<213> ORGANISM: Artificial Sequence
<220> FEATURE:
<223> OTHER INFORMATION: PRIMER

<400> SEQUENCE: 11
tgaatgaact gcaggacgag                                                  20

<210> SEQ ID NO 12
<211> LENGTH: 20
<212> TYPE: DNA
<213> ORGANISM: Artificial Sequence
<220> FEATURE:
<223> OTHER INFORMATION: PRIMER

<400> SEQUENCE: 12
gggtgttctg ctggtagtgg                                                  20
```

ENGINEERING RUBBER PRODUCTION IN PLANTS

REFERENCE TO RELATED APPLICATIONS

This application claims priority to U.S. Provisional Patent Application U.S. Ser. No. 61/789,228, filed Mar. 15, 2013, which is incorporated herein by reference in its entirety.

FIELD OF THE INVENTION

In exemplary embodiments the invention relates to transformation of *Parthenium argentatum* Gray (guayule) chloroplasts and to transformed *Parthenium argentatum* capable of producing increased amounts of natural rubber.

BACKGROUND OF THE INVENTION

*Parthenium argentatum* Gray commonly known as guayule, is a shrub in the family Asteraceae, native to the southwestern United States and northern Mexico. *P. argentatum* produces high quality rubber in bark tissue and finds particular value as an alternative source of natural rubber latex.

Natural rubber, cis-1,4-polyisoprene, is essential and irreplaceable in many industrial applications. Because of its desirable properties, the demand for natural rubber is rising, making natural rubber increasingly more precious as an industrial material. To meet demand at sustainable costs, it is desirable to increase the quantity and/or quality of natural latex rubber produced from guayule. Indeed, increasing the quantity of available natural rubber latex will benefit agricultural workers and many industries and thus, humankind in general.

Accordingly, discovering and developing guayule cultivars capable of producing high yields of natural rubber latex would be invaluable for increasing available quantities of natural rubber. Therefore, what is needed in the art, are methods for improving the quantity and/or quality of natural latex rubber from guayule, and new guayule cultivars capable of producing high yields of natural rubber latex.

Fortunately, as will be clear from the following disclosure, the present invention provides for these and other needs.

SUMMARY OF THE INVENTION

In one aspect, the present disclosure provides a method for transforming guayule chloroplasts to provide a transplastomic guayule plant, the method comprising: (i) growing guayule plants on hormone free media supplemented with activated charcoal to provide cultured guayule plants; (ii) collecting leaves from the cultured guayule plants to provide leaves from the cultured guayule plants; (iii) placing the leaves from the cultured guayule plants in medium comprising trans-zeotin-riboside for bombarding and recovery; (iv) bombarding the leaves from the cultured guayule plants with gold particles, wherein the gold particles are coated with chloroplast transformation vector DNA, and wherein the chloroplast transformation vector DNA comprises guayule specific flanking sequences that target insertion of the chloroplast transformation DNA to chloroplast DNA, thereby providing bombarded guayule leaves; (v) incubating the bombarded guayule leaves in the medium comprising trans-zeotin-riboside, to provide recovered bombarded guayule leaves; (vi) transferring the recovered bombarded guayule leaves to Callus and Shoot Induction medium comprising a selection agent and calcium nitrate; (vii) growing the recovered bombarded guayule leaves in Callus and Shoot Induction medium to provide calli and small shoots; (viii) transferring the calli and small shoots to Shoot Induction Medium wherein the Shoot Induction Medium comprises calcium nitrate; (ix) growing the calli and small shoots in the Shoot Induction Medium until shoots are elongated, to provide elongated shoots; (x) transferring the elongated shoots to Rooting Medium comprising a selection agent; (xi) growing the elongated shoots on the Rooting Medium until roots are formed, to provide rooted shoots; (xii) transplanting the rooted shoot to soil, and (xiii) growing the rooted shoots in the soil; thereby providing a transplastomic guayule plant. In one exemplary embodiment, the chloroplast transformation vector DNA further comprises the 6-gene cluster comprising the complete cytosolic mevalonate pathway.

In another aspect, the disclosure provides a transplastomic guayule plant made according to the method for transforming guayule chloroplasts to provide a transplastomic guayule plant. In one exemplary embodiment, the transplastomic guayule plant comprises recombinant chloroplasts transformed with the 6-gene cluster comprising the complete cytosolic mevalonate pathway. In another exemplary embodiment, the transplastomic guayule plant is capable of producing increased amounts of isopentenyl pyrophosphate and increased amounts of natural latex. In another exemplary embodiment, the disclosure provides a transplastomic seed of the transplastomic guayule plant. In another exemplary embodiment, the disclosure provides a transplastomic guayule plant, or a part thereof, produced by growing the seed. In another exemplary embodiment, the disclosure provides a tissue culture of regenerable transplastomic cells produced from the transplastomic guayule plant. In another exemplary embodiment, the disclosure provides a transplastomic protoplast produced from the tissue culture. In another exemplary embodiment, the disclosure provides a transplastomic guayule plant, regenerated from the tissue culture. In another exemplary embodiment, the disclosure provides a hybrid transplastomic guayule plant, wherein the lineage of at least one parent plant comprises the transplastomic guayule plant.

In another aspect the disclosure provides a transplastomic guayule plant or part thereof. In one exemplary embodiment, the the transplastomic guayule plant comprises recombinant chloroplasts transformed with the 6-gene cluster comprising the complete cytosolic mevalonate pathway. In another exemplary embodiment, the transplastomic guayule plant is capable of producing increased amounts of isopentenyl pyrophosphate and increased amounts of natural latex. In another exemplary embodiment, the disclosure provides a transplastomic seed of the transplastomic guayule plant. In another exemplary embodiment, the disclosure provides a transplastomic guayule plant, or a part thereof, produced by growing the seed. In another exemplary embodiment, the disclosure provides a tissue culture of regenerable transplastomic cells produced from the transplastomic guayule plant. In another exemplary embodiment, the disclosure provides a transplastomic protoplast produced from the tissue culture. In another exemplary embodiment, the disclosure provides a transplastomic guayule plant, regenerated from the tissue culture. In still another exemplary embodiment, the disclosure provides a hybrid transplastomic guayule plant, wherein the lineage of at least one parent plant comprises the transplastomic guayule plant.

Other features, objects and advantages of the invention will be apparent from the detailed description which follows.

BRIEF DESCRIPTION OF THE DRAWINGS

Figure 1A:
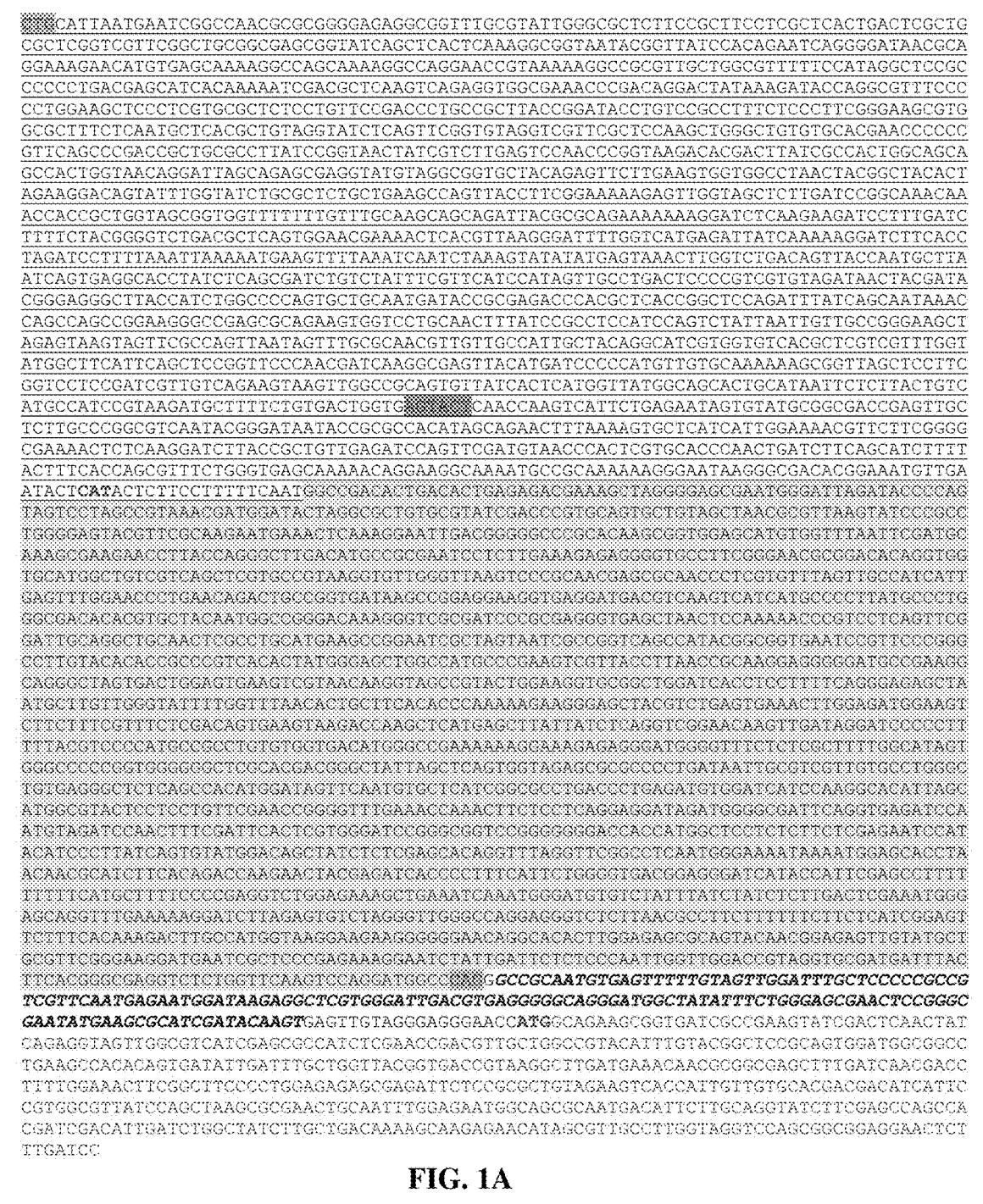
Figure 1B:
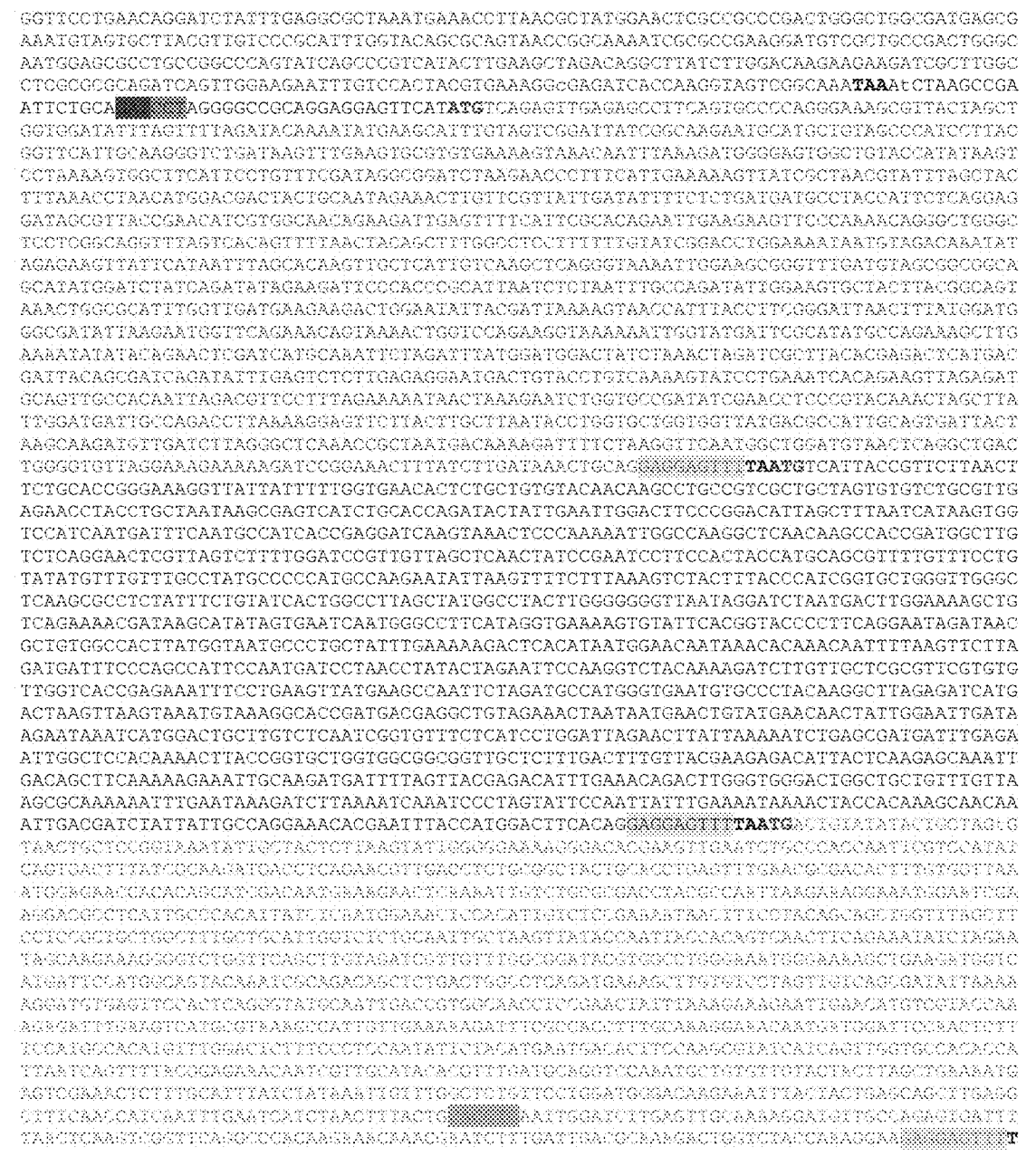
Figure 1C:
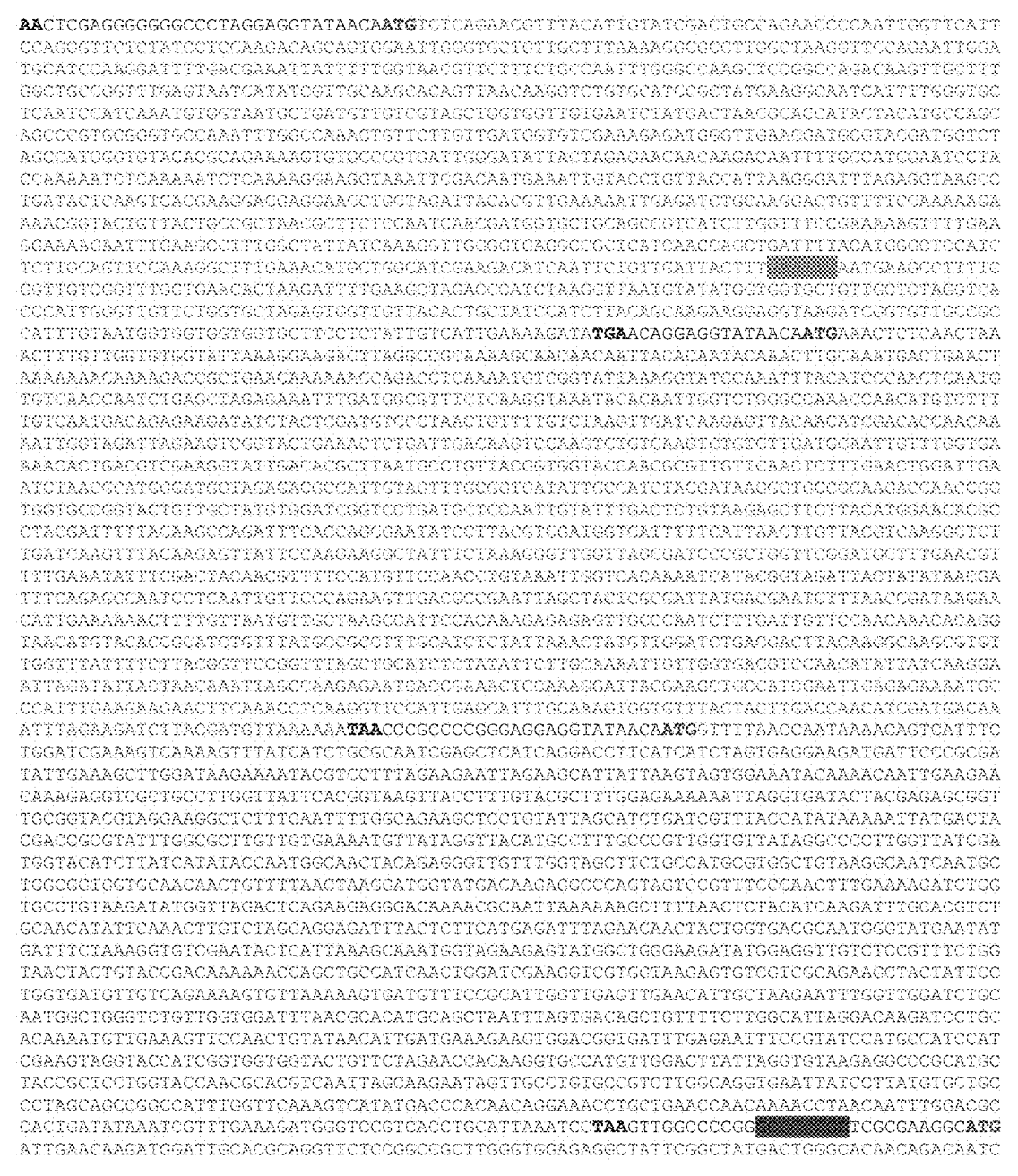
Figure 1D:
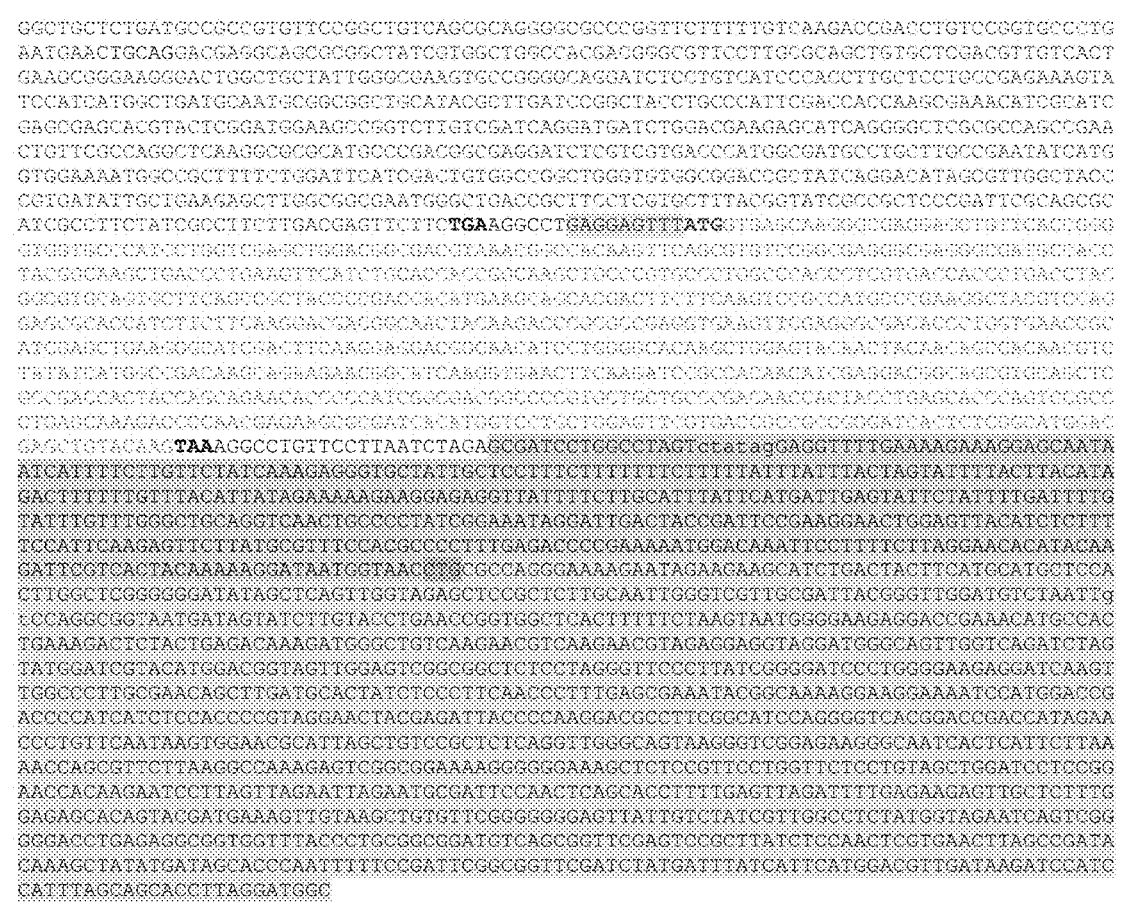

FIG. 1A, FIG. 1B, FIG. 1C, and FIG. 1D show SEQ ID NO:1, the nucleic acid sequence of a plastid transformation vector pUY-MEV6 comprising full length synthetic operon encoding the complete cytosolic mevalonate pathway.
Key:
TGCCATCC . . . and at end . . . GGGAGAGG all part of original backbone plasmid pUC19.
AGTACT=restriction enzyme ScaI cutting site
bp (1 . . . 1873)=ampicillin resistance gene in pUC19 (not used by us)
CAT=start codon for ampicillin resistance gene
bp (1874 . . . 3821)=guayule-specific flanking sequence
CAG - - - CTG=cutting site for PvuII, this is where the cassette(s) was inserted in between flanking sequences.
bp (3823 . . . 3973)=rrn16 promoter promoter for spectinomycin-resistance gene
bp (3993 . . . 4784)=spectinomycin-resistance gene
TAA=stop codon for spec resistance gene
GAAATTCA=rps16 terminator for spectinomycin-resistance gene
GATATC,=EcoRV GCGGCCGC=NotI, cutting sites used for MEV6
bp (4832 . . . 6203)=Scer PMK Phosphomevalonate kinase gene
bp (6203 . . . 7546)=Scer MVK Mevalonate kinase gene
bp (7546 . . . 8745)=Scer MDD mevalonate diphosphate decarboxylase gene
bp (8775 . . . 9971)=Scer AAct acetoacetyl coA thiolase gene
bp (9987 . . . 11462)=Scer HMGS HMGCoA synthase gene
bp (11487 . . . 12995)=Scer HMGRt HMGCoA reductase gene
TTCTGT=psbA promoter for KAN gene
bp (13025 . . . 13819)=kanamycin-resistance gene
bp (13835 . . . 14554)=GFP gene
bp (14576 . . . 14767)=terminator for GFP gene
GCCGGC ACTAGT GAATTC CATATG CTGCAG AGGCCT TCTAGA=various cutting sites, not used here.

FIG. 6 B: PCR amplification with aadA-GFP gene primers (forward 5'-TGAATGAACTGCAGGACGAG-3', SEQ ID NO:4 primers and reverse 5'-GGGTGTTCTGCTGG-TAGTGG-3', SEQ ID NO:5). Lane 1: 1 Kb marker, lane 2: plasmid DNA, lane 3: non-transgenic control plant, lanes 4 and 5: pUY-Gua-aadA/NPTII/GFP transgenic plants (1.2 kb).

DETAILED DESCRIPTION OF THE INVENTION

Definitions

Figure 2:
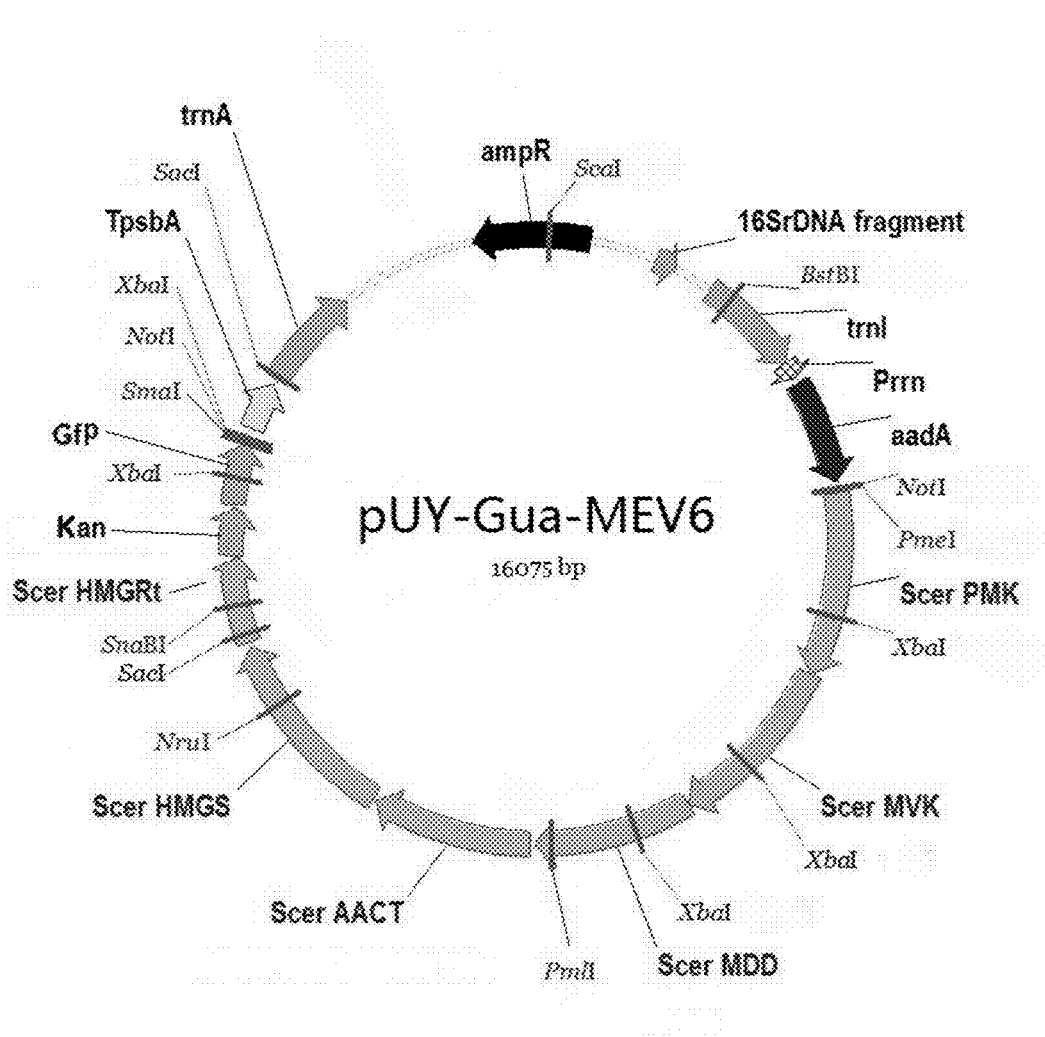
FIG. 2. Provides a diagrammatic representation of pUY-MEV6 shown as SEQ ID NO:1 in FIG. 1. To make pUY-Gua-MEV6, the 6-gene cluster comprising the complete mevalonate pathway from pUY-MEV6 (see e.g. Kumar et al. 2012 Metab Eng. 2012 January; 14(1):19-28) was used to replace the Trps 16 and the PpsbA-5' UTR in plasmid pUY-Gua-aadA/NPTII/GFP, resulted a the final plasmid containing 9 genes and 16075 bp.

The expression "capable of producing increased amounts of isopentenyl pyrophosphate" as used herein, refers to the ability of a transplastomic guayule plant as disclosed herein, to biosynthesize at least about 25% or more isopentenyl pyrophosphate (IPP) than is produced from an otherwise isogenic non-transplastomic guayule plant.

The expression "complete cytosolic mevalonate pathway" as used herein refers to an isoprenoid synthetic pathway located in the cytosol of animals, plants and fungi e.g., yeast, which produces isopentenyl pyrophosphate (IPP) condensation of three molecules of acetyl coenzyme A (CoA). The six genes that comprise the complete cytosolic mevalonate pathway are: acetoacetyl-CoA synthase, 3-hydroxy-3-methylglutaryl-CoA (HMG-CoA) synthase, HMG-CoA reductase, mevalonate kinase, phosphomevalonate kinase, and pyrophosphomevalonate decarboxylase.

The expression "capable of producing increased amounts of isopentenyl pyrophosphate and increased amounts of natural latex" as used herein, refers to the ability of plants to biosynthesize at least about 25% or more natural rubber than is produced from an otherwise isogenic non-transplastomic guayule plant.

The term "synthetic operon" as used herein, refers to a DNA sequence that comprises multiple individual genes which are expressed under the control of a single regulatory signal or promoter. An operon is "synthetic" by virtue of the fact that it is constructed in vitro, rather than being naturally occurring. Thus, in an exemplary embodiment, the six yeast genes that comprise the complete cytosolic mevalonate pathway are cloned into an expression vector to create a "synthetic operon" that encodes the complete cytosolic mevalonate pathway.

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to the broad class of higher plants amenable to transformation techniques. The term "plant" also includes plants of any variety of ploidy levels, including polyploid, diploid, haploid and hemizygous. Exemplary plants include e.g., dicotyledonous plants of the family Asteraceae e.g., *Parthenium argentatum*.

The term "transplastomic plant" as used herein refers to a plant comprising at least one heterologous nucleic acid sequence that was introduced into the plant chloroplasts, at some point in its lineage, by genetic engineering techniques. In an exemplary embodiment, a transplastomic plant is a plant whose plastids are transformed with an expression vector comprising a synthetic operon that encodes the six enzymes that comprise the complete cytosolic mevalonate pathway. In another exemplary embodiment, a transplastomic plant is a plant whose plastids are transformed with an expression vector comprising a synthetic operon that encodes the HMG-CoA reductase (HMGR). In another exemplary embodiment, a transplastomic plant is a plant that is the progeny or decendant of a transplastomic plant transformed with an expression vector comprising a synthetic operon that encodes the six enzymes that comprise the complete cytosolic mevalonate pathway, wherein the progeny or decendant is a transplastomic plant whose plastids contain the synthetic operon that encodes the six enzymes that comprise the complete cytosolic mevalonate pathway. Thus, the term "transplastomic plant" refers to plants which are the direct result of transformation with a heterologous nucleic acid or transgene, and the progeny and decendants of transformed plants which themselves comprise the introduced heterologous nucleic acid or transgene.

The terms "isolated," "purified," or "biologically pure" as used herein, refer to material that is substantially or essentially free from components that normally accompany it as found in its native state. In an exemplary embodiment, purity and homogeneity are determined using analytical chemistry techniques such as polyacrylamide gel electrophoresis or high performance liquid chromatography. A nucleic acid that is the predominant species present in a preparation is substantially purified. In one exemplary embodiment, an isolated nucleic acid or a fragment thereof is separated from open reading frames and/or other nucleic acid sequences that flank the nucleic acid or a fragment thereof in its native state. In an exemplary embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide" and "protein" are used interchangeably herein to refer to a polymer of amino acid residues. The terms apply to naturally occurring amino acid polymers and non-naturally occurring amino acid polymers as well as amino acid polymers in which one or more amino acid residues is an artificial chemical mimetic of a corresponding naturally occurring amino acid.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, 7-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon is altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, Proteins (1984)). Such conservatively modified variants are in addition to and do not exclude polymorphic variants, interspecies homologs, and alleles.

The following eight groups illustrate some exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Macromolecular structures such as polypeptide structures are described in terms of various levels of organization. For a general discussion of this organization, see, e.g., Alberts et al., Molecular Biology of the Cell ($3^{rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "label" as used herein, refers to a composition detectable by spectroscopic, photochemical, biochemical, immunochemical, or chemical means. Exemplary labels include $^{32}P$, fluorescent dyes, electron-dense reagents, enzymes (e.g., as commonly used in an ELISA), biotin, digoxigenin, or haptens and proteins for which antisera or monoclonal antibodies are available.

As used herein a "nucleic acid probe or oligonucleotide" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "labeled nucleic acid probe or oligonucleotide" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically DNA oligonucleotides of at least about 15 nucleotides in length. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of a guayule chloroplast genome sequence nucleic acid or a cytosolic mevalonate pathway nucleic acid will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994, John Wiley & Sons). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells comprise and/or express genes that are not found within the native (non-recombinant) form of the cell or express native genes that are otherwise abnormally expressed, over expressed, under expressed or not expressed at all.

The term "promoter" or "promoter complex" or "promoter sequence" as used herein refers to an array of nucleic acid expression control sequences that direct transcription of a nucleic acid. As used herein, a "promoter" or "promoter complex" or "promoter sequence" comprises necessary nucleic acid sequences near the start site of transcription, such as, e.g., a polymerase II type promoter, a TATA element etc to "control" transcription of an operably linked nucleic acid. In some exemplary embodiments, a "promoter complex" or "promoter sequence" also includes distal enhancer or repressor elements, which can be, but are not necessarily located as much as several thousand base pairs from the start site of transcription. In other exemplary embodiments, "promoter" or "promoter complex" or "promoter sequence" includes sequences that facilitate transcription of an operably linked heterologous nucleic acid and/or expression of the final protein product of the heterologous nucleic acid e.g., intron sequence and/or intron and ubiquitin monomer sequences as disclosed herein.

As is well known in the art, a "constitutive" promoter is a promoter that is active under most environmental and developmental conditions. An "inducible" promoter is a promoter that is active under environmental or developmental regulation, e.g., upregulation in response to wounding of plant tissues. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a guayule chloroplast genome sequence nucleic acid e.g., a guayule DNA barcode sequence. Hybridization of the first and second nucleic acids is conducted under standard stringent conditions, e.g., high temperature and/or low salt content, which tend to disfavor hybridization of dissimilar nucleotide sequences.

The term "operably linked" refers to a functional linkage between a nucleic acid expression control sequence (such as e.g., a promoter, or array of transcription factor binding sites) and a second nucleic acid sequence (such as e.g., a nucleic acid encoding in a single operon the six enzymes comprising the complete cytosolic mevalonate pathway) wherein the expression control sequence directs expression e.g., transcription, of the nucleic acid corresponding to the second sequence. In an exemplary embodiment, a promoter that is "operably linked" to a heterologous nucleic acid is located upstream of and in-frame with the heterologous nucleic acid.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a synthetic operon encoding the complete cytosolic mevalonate pathway. Similarly, a heterologous protein indicates that the protein comprises two or more subsequences that are not found in the same relationship to each other in nature (e.g., a fusion protein).

An "expression cassette" as used herein, refers to a nucleic acid construct, typically generated recombinantly or synthetically, which comprises a series of specified nucleic acid elements that permit transcription of a particular nucleic acid in a host cell. In an exemplary embodiment, an expression cassette comprises a heterologous nucleic acid to be transcribed e.g., a synthetic operon encoding the six genes encoding enzymes comprising the complete cytosolic the mevalonate pathway operably linked to a promoter.

Typically, an "expression cassette" is part of an "expression vector". The term "vector" as used herein, refers to nucleic acid capable of replicating in a selected host cell or organism. A vector can replicate as an autonomous structure, or alternatively can integrate into the host cell chromosomes and thus replicate along with the host cell genome. In some exemplary embodiments, an expression vector is integrated into the host cell chromosomes in its entirety. In other exemplary embodiments, a fragment of the expression vector e.g., the expression cassette and flanking sequences, is integrated into the host cell chromosome. Thus, an "expression vector" is a nucleic acid capable of replicating in a selected host cell or organism e.g., a plasmid, virus, artificial chromosome, nucleic acid fragment, or any suitable construct known in the art, which comprises an "expression cassette".

The term "transformation" as used herein encompasses any and all techniques by which a nucleic acid molecule might be introduced into a cell, including but not limited to, transfection with viral vectors, transformation with plasmid vectors, and introduction of naked DNA by electroporation, lipofection, *Agrobacterium* infection, and particle gun acceleration, etc. The term "transformation" as used herein applies to plants or plant parts e.g, leaf tissue, callous, chloroplasts, such that one obtains a transgenic plant e.g., a transplastomic plant. The term "transformation" as used herein also refers to the transformation of chloroplasts such that one obtains transgenic plants that are transplastomic plants.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length guayule chloroplast genome sequence, a segment of guayule DNA barcode sequence or gene sequence, or gene sequence given in a sequence listing, or may comprise a complete guayule chloroplast genome sequence, guayule DNA barcode sequence, or gene sequence.

The terms "identical" or percent "identity," in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, the substantial identity exists over a region of the sequences that is at least about 50 residues in length. In another exemplary embodiment, the substantial identity exists over a region of the sequences that is at least about 100 residues in length. In still another exemplary embodiment, the substantial identity exists over a region of the sequences that is at least about 150 residues or more, in length. In one exemplary embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An exemplary algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc. Acids Res. 12:387-395 (1984).

Another example of algorithm that is suitable for determining percent sequence identity and sequence similarity are the BLAST® and BLAST® 2.0 algorithms (Basic Local Alignment Search Tool), which are described in Altschul et al., Nuc. Acids Res. 25:3389-3402 (1977) and Altschul et al., J. Mol. Biol. 215:403-410 (1990), respectively. Software for performing BLAST® analyses is publicly available through the National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T, and X determine the sensitivity and speed of the alignment. The BLASTN® program (for nucleotide sequences) uses as defaults a wordlength (W) of 11, an expectation (E) or 10, M=5, N4and a comparison of both strands. For amino acid sequences, the BLASTP® program uses as defaults a wordlength of 3, and expectation (E) of 10, and the BLOSUM62 scoring matrix (see Henikoff & Henikoff, Proc. Natl. Acad. Sci. USA 89:10915(1989)) alignments (B) of 50, expectation (E) of 10, M=5, N=4, and a comparison of both strands.

The BLAST® algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST® algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

I. Introduction:

Natural rubber is a raw material vital to industry, transportation, medicine and defense. *Parthenium argentatum* Gray (guayule) produces high quality, rubber in its bark parenchyma and thus, there is considerable interest in developing guayule as a source of natural rubber latex.

Thus, in an exemplary embodiment the invention provides a transplastomic guayule plant comprising chloroplasts engineered to express the complete cytosolic mevalonate (MEV) pathway. These transplastomic plants are capable of producing increased amounts of isopentenyl pyrophosphate (IPP) and other isoprenoid pathway products e.g., terpenoids, sterols, carotenoids, phytohormones such as abscisic acid, squalene, and dolichols.

In some exemplary embodiments, a transplastomic guayule plant comprising chloroplasts engineered to express the complete cytosolic mevalonate (MEV) pathway capable of producing increased amounts of isopentenyl pyrophosphate (IPP) produces increased amounts of natural rubber as compared to a non-transplastomic guayule plant.

Isoprenoid biosynthetic pathways are responsible for the formation of the most chemically diverse family of metabolites found in nature, including sterols (C30), carotenoids (C40), dolichols (C40-50), ubiquinones (C30-50), and natural rubber (C2,000-300,000).

As is known in the art, isopentenyl pyrophosphate (IPP) and dimethylallyl diphosphate (DMAPP), are the two 5-carbon isoprenoid building-blocks from which most isoprenoids are built. Their synthesis occurs by two distinct routes in plants, in the cytosol and in plastids (see e.g., Bick, J.A. & Lange, B.M. (2003) *Arch. Biochem. Biophys.* 415: 146-154; Cornish, K., and Scott, D.J. (2005) Industrial Crops and Products 22 (2005) 49-58). In the cytosol, IPP and DMAPP are assembled from three molecules of acetyl Co-A by the mevalonate (MEV) pathway. In plastids, an independent pathway, called the 2-C-methyl-D-erythritol 4-phosphate (MEP) pathway, makes IPP and DMAPP from pyruvate and glyceraldehyde 3-phosphate.

Without being bound by theory it is believed that because the efficiency of nuclear transformation and especially chloroplast transformation is so low in guayule it is not possible to make or find transformants capable of producing increased amounts of natural rubber by comparison to wild type. Fortunately however, the inventors now disclose herein methods for chloroplast transformation of guayule which permit the construction of transplastomic guayule plants comprising chloroplasts engineered to express the complete cytosolic mevalonate (MEV) pathway. These transplastomic plants are capable of producing increased amounts of isopentenyl pyrophosphate (IPP) and natural rubber. In some exemplary embodiments, a transplastomic guayule plant comprising chloroplasts engineered to express the complete cytosolic mevalonate (MEV) pathway capable of producing increased amounts of isopentenyl pyrophosphate (IPP) produces increased amounts of natural rubber as compared to a non-transplastomic guayule plant.

II. Isolating the Guayule Chloroplast Genomic DNA the Complete Cytosolic Mevalonate (MEV) Pathway Nucleic Acids and Constructing Expression Vectors A. General Recombinant DNA Methods This invention utilizes routine techniques in the field of recombinant genetics. Basic texts disclosing the general methods of use in this invention include Sambrook et al., Molecular Cloning—A Laboratory Manual (2nd Ed.), Vol. 1-3, Cold Spring Harbor Laboratory, Cold Spring Harbor, N.Y., 1989; Kriegler, Gene Transfer and Expression: A Laboratory Manual (1990); and Current Protocols in Molecular Biology (Ausubel et al., eds., 1994)). Unless otherwise noted, technical terms are used according to conventional usage. Definitions of common terms in molecular biology maybe found in e.g., Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized e.g., according to the solid phase phosphoramidite triester method first described by Beaucage & Caruthers, Tetrahedron Letts. 22:1859-1862 (1981), using an automated synthesizer, as described in Van Devanter et al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Methods for the Isolation of Cytosolic Mevalonate Pathway Genes and Guayule Chloroplast Genome Sequence Nucleic Acids

*Parthenium argentatum* Gray commonly known as guayule, is a shrub in the family Asteraceae, native to the southwestern United States and northern Mexico. *P. argentatum* produces high quality rubber in bark tissue and finds particular value as a source of natural rubber latex. Indeed, guayule is an important source of natural rubber latex that is safe for people with Type I latex allergy.

Guayule chloroplast genome sequence nucleic acids, and cytosolic mevalonate pathway genes can be isolated using any of a variety of methods known to those of skill in the art which may be used for isolation of chloroplast genome sequence nucleic acids. For example, guayule chloroplast genome sequence nucleic acids can be isolated from a guayule genomic library and/or from a guayule chloroplast genomic library.

Similarly, cytosolic mevalonate pathway genes can be isolated using any of a variety of methods known to those of skill in the art which may be used for isolation of genome sequence nucleic acids.

Genomic fragments can be prepared as disclosed below.

To prepare a genomic library, typically DNA is extracted from plant tissue and either mechanically sheared or enzymatically digested to yield fragments of about 15-20 kb. The fragments are then separated by gradient centrifugation from undesired sizes and are constructed in bacteriophage lambda vectors. These vectors and phage are packaged in vitro, as described e.g., in Sambrook, et al. supra. Recombinant phage are analyzed by plaque hybridization as described in Benton and Davis, Science, 196:180-182 (1977). Colony hybridization is carried out as generally described in M. Grunstein et al. Proc. Natl. Acad. Sci. USA., 72:3961-3965 (1975). DNA sequences encoding the complete cytosolic mevalonate pathway and/or fragments thereof, are identified in genomic libraries by the ability of the sequences to hybridize with labeled nucleic acid probes that comprise sequences which encode one or more individual genes (or fragments thereof) that comprise the cytosolic mevalonate pathway, e.g., on Southern blots. The hybridizing DNA regions are isolated by standard methods familiar to those of skill in the art. See e.g., Sambrook, et al. supra.

Other methods known to those of skill in the art can also be used to isolate sequences encoding the complete cytosolic mevalonate pathway. See e.g., Sambrook, et al. for a description of other techniques for the isolation of DNAs related to DNA molecules of known sequence.

Sequence Features of Sequences Encoding the Complete Cytosolic Mevalonate Pathway The genes encoding enzymes comprising the complete cytosolic mevalonate pathway from yeast and a synthetic operon comprising all six cytosolic mevalonate pathway genes are known in the art (see e.g., U.S. Pat. No. 7,129, 392). The sequence of a plastid transformation vector comprising full length synthetic operon encoding the complete cytosolic mevalonate pathway is also shown in FIG. 1, as SEQ ID NO:1. A diagrammatic representation of the nucleic acid sequence illustrated in FIG. 1. Is provided in FIG. 2.

The transformation vector includes guayule-specific flanking sequences to allow site-specific insertion of the cassette.

The order of the six cytosolic mevalonate pathway genes on the transformation vector is: Phosphomevalonate kinase; Mevalonate kinase, mevalonate diphosphate decarboxylase, acetoacetyl co-A thiolase, HMGco-A synthase, HMGco-A reductase.

C. Construction of Vectors Comprising Sequences Encoding the Cytosolic Mevalonate Pathway Genes Once sequences encoding cytosolic mevalonate pathway enzymes have been isolated, various methods may be used to construct expression cassettes, vectors and other DNA constructs. Expression cassettes comprising sequences encoding the complete cytosolic mevalonate pathway can be constructed in a variety of ways. The skilled artisan is well aware of the genetic elements that must be present on an expression construct/vector in order to successfully transform, select and propagate the expression construct in host cells e.g., in chloroplasts, see e.g., Wu, S. et al. (2006) *Nat. Biotechnol.* 24:1441-1447; Maliga, P. (2004) *Annu. Rev. Plant Biol.* 2004. 55:289-313) Techniques for manipulation of nucleic acids encoding enzymes comprising the complete cytosolic mevalonate pathway such as subcloning nucleic acid sequences into expression vectors, labeling probes, DNA hybridization, and the like are described generally in Sambrook, et al., supra.

Although cytosolic mevalonate pathway genes can be individually cloned and expressed, in an exemplary embodiment, the six genes encoding cytosolic mevalonate enzymes acetoacetyl-CoA synthase, 3-hydroxy-3-methylglutaryl-CoA (HMG-CoA) synthase, HMG-CoA reductase, mevalonate kinase, phosphomevalonate kinase, and pyrophosphomevalonate decarboxylase, are cloned and expressed from a single synthetic operon (see e.g., U.S. Pat. No. 7,129,392; FIG. 1 and FIG. 2.).

DNA constructs comprising sequences encoding the complete cytosolic mevalonate pathway can be inserted into a variety of vectors. Typically, the vector chosen is a vector suitable for expressing the complete cytosolic mevalonate pathway in chloroplasts. An exemplary vector comprising a synthetic operon encoding the complete cytosolic mevalonate pathway is shown in FIG. 2. Such vectors can be constructed by the use of recombinant DNA techniques well known to those of skill in the art. See e.g., Sambrook et al. supra. An expression vector comprising e.g., a sequence encoding all six enzymes that comprise the complete cytosolic mevalonate pathway, may then be transfected/transformed into the target chloroplast/plastid. Successfully transformed plastids are then selected based on the presence of a suitable marker gene as disclosed below.

Figure 3:
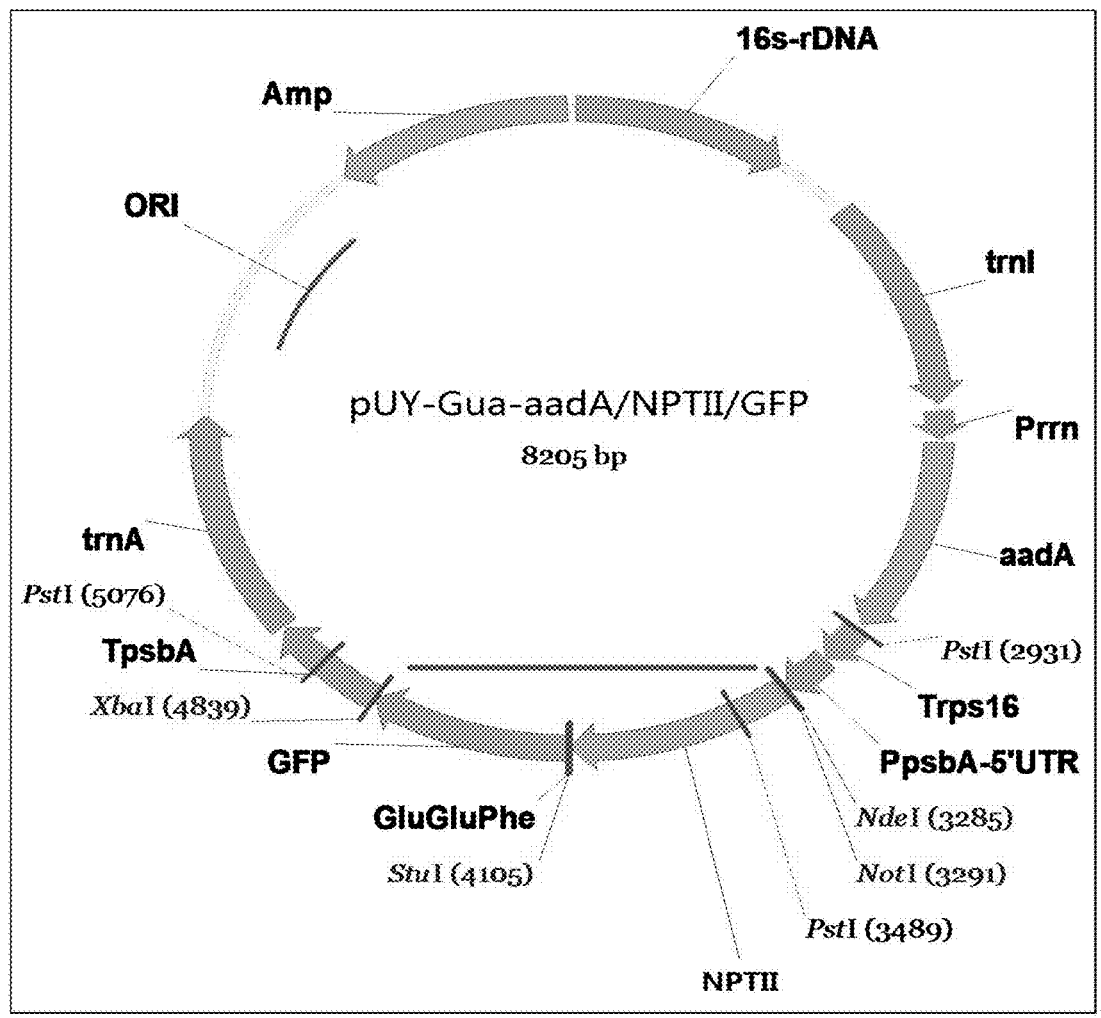
FIG. 3. Illustrates Guayule Specific Chloroplast transformation vector (pUY-Gua-aadA/NPTII/GFP).

A number of recombinant vectors are available to those of skill in the art for use in the stable transfection of chloroplasts for the establishment of transplastomic plants (see e.g., FIG. 3. In particular, recombinant vectors are available to those of skill in the art for use in the stable transfection of chloroplasts typically comprise homologous flanking sequences on either side of the transgene cassette to facilitate double recombination. The flanking sequences are generally about 1 kb in size. Chloroplast vectors may also carry an origin of replication that facilitates replication of the plasmid inside the chloroplast, thereby increasing the template copynumber for homologous recombination and consequently enhancing the probability of transgene integration.

(i) Elements

In addition to sequences encoding the complete cytosolic mevalonate pathway, expression constructs prepared as disclosed may comprise additional elements.

(ii) Marker Genes

As noted above, plastid transformation vectors typically include a selectable and/or screenable marker gene to allow for the ready identification of transformants. Exemplary selectable marker genes include, but are not limited to those encoding antibiotic resistance (e.g. resistance to hygromycin, kanamycin, bleomycin, G418, streptomycin or spectinomycin) and herbicide resistance genes (e.g., phosphinothricin acetyltransferase). Exemplary screenable markers include e.g., green florescent protein.

In an exemplary embodiment, a selectable or screenable marker gene is employed in addition to sequences encoding the complete cytosolic mevalonate pathway, to provide or enhance the ability to identify transformants. As is known in the art, "marker genes" are genes that impart a distinct phenotype to cells expressing the marker gene, such that transformed cells can be distinguished from cells that do not have the marker. In one exemplary embodiment, marker genes encode a selectable marker which one can "select" for by chemical means, e.g., through the use of a selective agent (e.g., a herbicide, antibiotic, or the like). In another exemplary embodiment, marker genes encode a screenable marker, which is identified through observation or testing, e.g., by "screening" (e.g., the green fluorescent protein).

Numerous selectable marker genes are known to the art. Some exemplary selectable markers are disclosed in e.g., Potrykus et al., (1985) Mol. Gen. Genet., 199:183-188; Stalker et al., (1988) Science, 242:419 422; Thillet et al., (1988) J. Biol. Chem., 263:12500 12508; Thompson et al., (1987), EMBO J 6:2519-2523; Deblock et al. (1987), EMBO J. 6:2513-2518; U.S. Pat. No. 5,646,024; U.S. Pat. No. 5,561,236; U.S. Patent application Publication 20030097687; and Boutsalis, P., and Powles, S. B. (1995) Weed Research 35: 149-155.

Some exemplary screenable markers include, but are not limited to a β-glucuronidase (GUS) or uidA gene, see e.g., U.S. Pat. No. 5,268,463, U.S. Pat. No. 5,432,081 and U.S. Pat. No. 5,599,670; a β-gene, see e.g., Sutcliffe, (1978) Proc. Natl. Acad. Sci. USA, 75:3737-3741); β-galactosidase; and luciferase (lux) gene (see e.g., Ow et al., (1986) Science, 234:856-859; Sheen et al., (1995) Plant J., 8(5):777-784; and WO 97/41228).

Exemplary selectable or screenable marker genes also include genes which encode a "secretable marker" whose secretion can be detected as a means of identifying or selecting for transformed cells. Exemplary secretable markers include but are not limited to secretable antigens that can be identified by antibody interaction, e.g., small, diffusible proteins detectable, e.g., by ELISA; and/or secretable enzymes which can be detected by their catalytic activity. E.g., small active enzymes detectable in extracellular solution (e.g., α-amylase, β-lactamase, phosphinothricin acetyltransferase); and proteins that are inserted or trapped in the cell wall (e.g., proteins that include a leader sequence such as that found e.g., in the expression unit of extensin or tobacco PR-S).

The choice of a particular marker gene is readily made by the skilled practitioner according to the needs and considerations of the particular application or use.

(iv) Other Vector Components

In some exemplary embodiments, an expression vector further comprises sequences that are joined to the sequences encoding the complete cytosolic mevalonate pathway, which are removed post-translationally from the initial translation product. In one exemplary embodiment, post-translationally removed sequences facilitate the transport of the protein into or through intracellular or extracellular membranes, thereby facilitating the transport of the protein into compartments inside and/or outside the cell. In an exemplary embodiment, post-translationally removed sequences protect a nascent protein from intracellular proteolytic degradation. In one exemplary embodiment, a nucleic acid segment encoding a leader peptide sequence upstream and in reading frame with a selected coding sequence is used in recombinant expression of the coding sequence in a host cell.

In another exemplary embodiment, an expression construct comprises a bacterial origin of replication, e.g., a colE1 origin. In still another exemplary embodiment, an expression construct/vector comprises a bacterial selectable marker e.g., an ampicillin, tetracyclin, hygromycin, neomycin or chloramphenicol resistance gene.

As is well known in the art, expression constructs typically comprise restriction endonuclease sites to facilitate vector construction. Exemplary restriction endonuclease recognition sites include, but are not limited to recognition site for the restriction endonucleases NotI, AatII, SacII, PmeI, HindIII, PstI, EcoRI, and BamHI.

D. Plant Hosts, Chloroplast Transformation and Plant Selection and Regeneration Techniques DNA constructs comprising a gene or a synthetic operon encoding all six genes comprising the complete cytosolic mevalonate pathway, can be transformed into plastids to provide transplastomic plants with desired phenotypic characteristics e.g., having the ability to produce increased amounts of natural rubber as compared to non-transplastomic plants. Exemplary plants for transformation with expression constructs comprising the complete cytosolic mevalonate pathway include, but are not limited to; dicotyledonous species, such as e.g., guayule (*Parthenium argentatum*); tobacco (*Nicotiana* spp.), *Lactuca* spp. and sunflower (*Helianthus* spp.).

In an exemplary embodiment, guayule (*Parthenium argentatum*) is transformed with a DNA construct that comprises a synthetic operon which encodes the six genes comprising the complete cytosolic mevalonate pathway.

Although plastid transformation in higher plants is known in the art (see e.g., Svab Z, et al. (1990). *Proc. Natl. Acad. Sci. USA* 87:8526-30; U.S. Patent Application Publication 2006/0248608; U.S. Patent Application Publication 2010/0218277). In general, chloroplast transformation is a routine procedure only in tobacco (see e.g., Maliga, P. (2004) Annu. Rev. Plant Biol. 2004. 55:289-313).

Therefore, before now it has not been possible to produce a transplastomic guayule plant comprising chloroplasts engineered to express the complete cytosolic mevalonic acid (MEV) pathway wherein the transplastomic guayule plants are capable of producing increased amounts of isopentenyl pyrophosphate (IPP), and ultimately increased amounts of rubber (see e.g., Liu et al., Plant Cell Rep 2007; Sikdar et al. (1998) Journal of Physiology 511, 851-859; Bogorad (2000) TIBTech 18:257-263; Verma and Danielle (2007); Plant Physiology 145:1129-1143. Indeed, it is generally accepted that the harder it is to transform any given species' nuclear DNA, all the more difficult it will be to transform the chloroplast. Guayule is considered difficult in nuclear transformation (under 2% efficiency usually) so for chloroplast transformation one might expect zero success or fractional percentage efficiencies at best.

Fortunately, the present inventors have discovered, and now herein disclose, reliable methods for the transformation of guayule chloroplasts (see e.g., Examples 2, 3 and 7) and regeneration of the transformed protoplasts thereby making it possible to produce a transplastomic guayule plant comprising chloroplasts engineered to express the complete cytosolic mevalonic acid (MEV) pathway. Such transformed guayule plants are capable of producing increased amounts of isopentenyl pyrophosphate (IPP), and increased amounts of natural rubber.

Exemplary aspects of the transformation and propagation methods disclosed herein which contribute to the success of the method include e.g.:

Media composition: Transformation media: MS (Murashige and Skoog, Murashige T and Skoog F (1962) Physiol Plant 15:473-497) media or DKW (Driver and Kuniyuki Walnut; Driver and Kuniyuki 1984)) media supplemented with calcium nitrate; and activated charcoal Propagation media: WPM (or Woody Plant Medium; Lloyd and McCown 1981) supplemented with activated charcoal.

When present, concentration of activated charcoal is typically at least about 0.2% w/v (or 2 g/L). However, in some exemplary embodiments, activated charcoal is present in concentration that is in a range that is between about 1 g/L to about 10 g/L. In other exemplary embodiments, activated charcoal is present in a concentration that is a range that is between about 1 g/L to about 5 g/L. Thus, in some exemplary embodiments, activated charcoal is present in a concentration that is about 1 g/L, about 2 g/L, about 3 g/L, about 4 g/L, about 5 g/L, about 6 g/L, about 7 g/L, about 8 g/L, about 9 g/L, or about 10 g/L.

When present, the concentration of calcium nitrate is typically at least about 100 mg/L. However, in some exemplary embodiments, calcium nitrate is present in a concentration that is in a range that is between about 100 mg/L to about 1500 mg/L. In other exemplary embodiments, calcium nitrate is present in a concentration that is about 150 mg/L, about 200 mg/L, about 250 mg/L, about 300 mg/L, about 350 mg/L, about 400 mg/L, about 450 mg/L, about 500 mg/L, about 550 mg/L, about 600 mg/L, about 650 mg/L, about 7000 mg/L, about 750 mg/L, about 800 mg/L, about 850 mg/L, about 900 mg/L, about 950 mg/L, about 1000 mg/L, about 1100 mg/L, about 1200 mg/L, about 1300 mg/L, about 1400 mg/L or about 1500 mg/L.

Zeatin shock: before and immediately after introducing the transgene, plants are exposed to high concentration of trans zeatin riboside (or similar chemicals as listed in table) Typical concentration of trans zeotin-riboside is at least about 5 mg/L. However, concentrations in a range that is between about 1 mg/L to about 160 mg/L are used effectively. Thus, in some exemplary embodiments trans-zeotin-riboside is present in a concentration of about 1 mg/L, about 3 mg/L, about 5 mg/L, about 10 mg/L, about 15 mg/L, about 20 mg/L, about 30 mg/L, about 40 mg/L, about 50 mg/L, about 60 mg/L, about 70 mg/L, about 80 mg/L, about 90 mg/L, about 100 mg/L, about 110 mg/L, about 120 mg/L, about 130 mg/L, about 140 mg/L, about 150 mg/L, or about 160 mg/L.

Dipping method for rooting: optimized exposure (conc and time) to plant hormone (IBA specifically) for rooting.

One of skill will recognize that, after an expression cassette is stably incorporated into chloroplasts and confirmed to be operable, a transplastomic plant is thereby provided. In one exemplary embodiment, an expression cassette comprising complete cytosolic mevalonic acid (MEV) pathway is stably incorporated into chloroplasts and confirmed to be operable, thereby providing a transplastomic plant having increased production of natural latex rubber. Transplastomic plants can be used to introduce the metabolically engineerered chloroplasts into new plants by sexual crossing, thereby developing new transplastomic lines. Any of a number of standard breeding techniques can be used, depending upon the species to be crossed.

The skilled artisan will recognize that multiple events may need to be screened in order to obtain lines displaying the desired expression level and pattern. Exemplary method for screening transformation events may be accomplished e.g., by PCR as disclosed hereinbelow; by Southern analysis of DNA blots (Southern, (1975) J. Mol. Biol. 98: 503), Northern analysis of mRNA expression (Kroczek, J., (1993) Chromatogr. Biomed. Appl., 618(1 2): 133 145), Western analysis of protein expression, and/or phenotypic analysis e.g., resistance to an herbicide can be detected by treatment with the herbicide. Expression of the heterologous DNA can also be detected by measurement of the specific RNA transcription product. This can be done by, for example, RNAse protection or Northern blot procedures. If heterologous DNA sequences encode a novel protein, the protein product may be assayed, for instance, by its function or by a variety of immunoassay techniques. Alternatively, a novel protein product with enzymatic activity can be measured in an enzyme assay. In another exemplary embodiment, protein expression is quantitated and/or detected in different plant tissues using a reporter gene, e.g., GUS.

Once transplastomic plants have been obtained, they may be grown to produce plant tissues or parts having the desired phenotype. The plant tissue or plant parts may be harvested, and/or the seed collected. The seed may serve as a source for growing additional plants with tissues or parts having the desired characteristics.

E. Detecting Expression of Heterologous Nucleic Acids in Transplastomic Plants

The introduction of expression vectors into chloroplasts as disclosed herein is useful for the introduction of one or more new traits to a host plant cell e.g., introducing a synthetic operon encoding the six genes that encode enzymes comprising the complete cytosolic mevalonate pathway and thereby providing a transplastomic guayule plant capable of producing increased amounts of isopentenyl pyrophosphate (IPP). There are a variety of different approaches one can use determine if a desired phenotype has been produced in transplastomic plants (see e.g., Kumar et al., Metabolic Engineering 14 (2012) 19-28).

In general, a transplastomic guayule plant is detected by means which include but are not limited to:

Growth on selection: a) In an exemplary embodiment, the independently-generated transplastomic lines are subjected to 4-6 rounds of regeneration on spectinomycin. Spectinomycin is an antibiotic that is fatal to guayule plants at about 12 mg/L. The aadA gene, included in the operon, confers resistance to spectinomycin. Plants that survive under spectinomycin selection pressure (12-20 mg/L) are putative transplastomic guayule. b) Regeneration on kanamycin. Kanamycin is an antibiotic that is also fatal to guayule. The NPTII gene, included in the operon, confers resistance to kanamycin. Plants that survive under selection pressure are possibly putatively transplastomic.

Genomic PCR analysis: To test integration of gene cassettes into the chloroplast genome, PCR is performed with primers that are targeted to one of the introduced genes (e.g., GFP, aadA, NPTII or other genes) and compared to the native chloroplast genomic DNA.

Green Fluorescent Protein detection: Transplastomic plant tissues with the GFP gene exhibit fluorescence when exposed to visible light. The emission peak is at 509 nm, which is in the lower green portion of the visible spectrum.

Leaf painting: Transformed plants expressing the antibiotic resistance genes should be resistant to antibiotics. To confirm that all parts of the plant have been transformed, leaf painting techniques can be used. This technique are used to detect and eliminate chimeric plants. In practice, various leaves from different sections of the plant are brushed/spotted with antibiotic solution, then inspected for browning over a period of time. This is preferably done on plants that have been transferred to soil. Plants exhibiting no browning on any leaf sections may be homoplasmic.

Genomic southern blot analysis: Southern blots are performed to analyze gene integration into the plant DNA. Total genomic DNA (2 mg) of transgenics and wildtype, are digested with appropriate restriction enzymes and hybridized with a P32-labeled DNAprobe amplified by the PCR using primers to internal regions of flanking native DNA.

Gene expression analysis: Performed by isolation of total RNA followed by addition of specific reverse-transcriptase primers targeted to specific genes or junctions of genes within the insert, followed by amplification by PCR and sequencing of the PCR products.

To functionally confirm the presence of the MEV6 genes, transplastomic and wildtype plants are grown on medium containing fosmidomycin at 100 mM. Fosmidomycin is a specific inhibitor of dxr in the plastidial MEP pathway (Zeidler et al., (1998) Z Naturforsch 53: 980-986). When dxr is inhibited in chloroplasts, the plastids no longer appear green, and turn white. If IPP is available through the alternative, inserted MEV6 pathway, the plant can use that IPP to produce chlorophyll and the tissues will appear green.

Analysis of metabolic pathway products: including sterols, fatty acids and triglycerides, carotenoids, squalene, and of course, natural rubber produced in the plants.

Measurement of the IPP levels in the plant is made according to methods known in the art see e.g.,: Mönkkönen, H., Auriola, S., Lehenkari, P., Kellinsalmi, M., Hassinen, I. E., Vepsäläinen, J. & Mönkkönen, J. A. (2006). British Journal of Pharmacology, 147, 437-445.

Detecting Increased Production of IPP and Natural Rubber

Natural rubber content of plants that grow successfully on selection media, and/or plants that test positive for the presence of the transgenes, is quantified vs. control plants. In an exemplary embodiment, natural rubber content is quantified by extraction of rubber in latex form, latex quantification, by methods known in the art (see e.g., Cornish et al, Industrial Crops and Products 10 (1999) 121-136) In another exemplary embodiment, natural rubber content is quantified by using solvent (e.g., toluene, cyclohexane, or THF) extraction of harvested, ground plant tissues by methods known in the art (Pearson et al, Industrial Crops and Products 31 (2010) 469-475). The quality of natural rubber is usually indicated by molecular weight and molecular weight distribution, as determined by gel permeation chromatography, well known to those skilled in the art (see e.g., Wyatt, P. J. 1993 Light scattering and the absolute characterization of macromolecules. Analytica Chimica Acta 272, 1-40; Jackson, C. et al., 1996 Size exclusion chromatography with multiple detectors: solution properties of linear chains of varying flexibility in tetrahydrofuran. Journal of Applied Polymer Science 61, 865-874).

In some exemplary embodiments, increased rubber concentration is accompanied by equivalent or increased concentration of resins and/or biomass.

The following examples are offered to illustrate, but not to limit the invention.

EXAMPLES

Example 1

The following example illustrates successful guayule chloroplast transformation.

Materials and Methods for Example 1

Plant Material

In vitro cultures of guayule were established from seeds of cultivar AZ-2 obtained from the USDA-ARS US-Arid Lands Research Center (Maricopa, Ariz.). Seeds were excised, then soaked sequentially in a 2% Tween-20 solution for 5 min, 70% ethanol for 1 min and in a 0.525% sodium hypochlorite (Clorox®) solution for 15 min. Seeds were triple rinsed with sterile water for 5 min each time. After germination, 3 cm of shoot tip was placed into a ma magenta box containing 88 mL of Murashige and Skoog (MS) (1962) basal medium supplemented with MS vitamins (PhytoTechnology Laboratories, Shawnee Mission, Kans.), 3% (w/v) sucrose and 0.3% (w/v) phatagel (Cat. No. p8169, Sigma). The solution was adjusted to pH 5.7-5.8 prior to autoclaving at 121° C. and 103.5 kPa (15 lb in-2) for 30 min. This was the established medium used to maintain in vitro guayule cultures in our laboratory (Dong et al, 2006). The cultures were maintained in a growth chamber at 25° C. under a 16-h photoperiod provided by cool-white fluorescent lamps. The lamps provided a photosynthetic photon flux of 125 $\mu mol \cdot m^{-2} \cdot s^{-1}$, held at the top of the culture vessels. All of the stock cultures in the following experiment were maintained under these conditions.

Propagation of Guayule Explants

In vitro guayule shoots were cultured aseptically on woody plant medium (WPM) (Lloyd and McCown (1981) Combined Proceedings—International Plant Propagator's Society, 30: 421-427) without any plant growth regulator (PGR). Vigorously growing ~3 cm shoot tips were excised for guayule propagation as disclosed hereinbelow in Examples 1 and 6.

All medium were supplemented with 0.1% MS vitamins, 3% (w/v) sucrose, 0.2% Activated charcoal (w/v) and 0.3% (w/v) phatagel (Sigma).

Resistance of Regenerated Shoot on Spectinomycin Media

To confirm whether the guayule explants were resistant to spectinomycin, in vitro leaf explants from control plants were cultured on regeneration DKW media that contained 0.75 mg·L⁻¹ BA and 0.25 mg·L⁻¹ NAA at 12 mg·L⁻¹ spectinomycin antibiotic levels.

Vector and E. coli Strain

The plasmid transformation vectors used in this work were pUY-Gua-aadA/NPTII/GFP. The plasmid pUY-Gua-aadA/NPTII/GFP vector (FIG. 3) contains the aadA (aminoglycoside 3-adenyl transferase) and NPTII gene as a selectable, and the multiple cloning site flanked guayule plastid DNA homologous sequences to target the insertion of the linked transgenes into the plastid genome by homologous recombination. Also plasmid contained the green fluorescent protein (GFP). The aadA and NPTII gene encodes resistance to spectinomycin and kanamycin, respectively.

All cloning steps were carried out in *E. coli* according to the methods of Sambrook et al (1989).

Transformation of Guayule

For transformation, young leaves were harvested from 4 weeks old plants produced from outgrowing axillary meristems in stem cutting. The vigorous young leaves were placed in media (MSZ5 media) for bombardment and recovery. The leaves were then bombarded with gold particles of 0.6 mm in diameter coated with pUY-Gua-aadA/NPTII/GFP plasmid, using a PDS 1000/He Biolistic® (Bio-Rad, Hercules, Calif.) device employing 1100 psi rupture disks and a target distance of 6 cm. In each bombardment, 0.7 mg of 0.6 micron gold and 12.5 ug of plasmid DNA were used. After bombardment, guayule explants were cultured at 25° C. in growth chamber for 5 days on the MSZ5 medium (MS medium supplemented with 5 mg·L$^{-1}$ trans zeatin riboside) for recovering.

To select an optimal medium for callus and shoot formation, DKW medium were used. Recovered explants were transferred onto DKW-CN-SP12 (DKW medium supplemented with 0.75 mg·L$^{-1}$ N6 benzylaminopurine (BA), 0.25 mg·L$^{-1}$ α-naphthaleneacetic acid (NAA), 250 mg·L$^{-1}$ calcium nitrate and 12 mg·L$^{-1}$ spectinomycin) selection medium for callus and shoots induction. After 6 weeks later, the regenerated green shoots were transferred onto the new DKW-CN-SP15 (DKW medium supplemented with 0.75 mg·L$^{-1}$ N6 benzylaminopurine (BA), 0.25 mg·L$^{-1}$ α-naphthaleneacetic acid (NAA), 250 mg·L$^{-1}$ calcium nitrate and 15 mg·L$^{-1}$ spectinomycin) to remove chimerical shoots and for selection of resistant and elongation shoots for 6 weeks. Every 3 weeks the callus and explants were transferred to the new fresh plates of the same media types. Regenerated shoot transferred to rooting medium (WP medium supplement with 0.2 mg·L$^{-1}$ IBA and 12 mg·L$^{-1}$ spectinomycin) when it grow up over 2 cm.

All in vitro explants were aseptically grown on MS or DKW supplemented with 0.1% MS vitamins, 3% (w/v) sucrose and 0.3% (w/v) phatagel (Sigma).

In general the method disclosed herein differs from known methods in: 1) media composition (transformation and propagation, 2) the use of cytokinin shock, 3) Dipping method for rooting. The bombardment conditions used were pretty standard.

Our observation is that for plants are growing on media containing activated charcoal, the chlorophyll A content is apparently increased (greener). Without being bound by theory it is believed that the chloroplasts are healthier, or more numerous, or both. Accordingly, the health of the chloroplasts could be one reason for the success of the method.

Furthermore, Cytokinins (CK) e.g., zeatin, are naturally-occurring secondary metabolites that function in plant growth, development, and signaling (see e.g., Hitoshi Sakakibara (2006) Cytokinins: Activity, Biosynthesis, and Translocation Annu. Rev. Plant Biol. 57:431-449). The specific nature of these interactions is not completely understood. However, including Zeatin in the media before and after bombardment clearly contributes to the success of the method.

Thus, the transformation methods disclosed herein in Example 1, 2 and 6 utilize the following elements for successful guayule chloroplast transformation: 1) Media composition: (a) Transformation media: MS (Murashige and Skoog, Murashige T and Skoog F (1962) Physiol Plant 15:473-497) media or DKW (Driver and Kuniyuki Walnut; Driver and Kuniyuki 1984) media supplemented with calcium nitrate. (b) Propagation media: WPM (Woody Plant Medium; Lloyd and McCown 1981) supplemented with activated charcoal.

2.) Cytokinin (Zeatin) shock: before and immediately after introducing the transgene, plants are exposed to high concentration of trans zeatin riboside (or similar chemicals as listed in table).

3.) Dipping method for rooting: optimized exposure (conc and time) to plant hormone (IBA specifically) for rooting.

DNA Extraction and PCR Amplification

Total DNA was extracted from 100 mg leaf tissues of the transformed and wild type guayule plants. The Polymerase chain reaction (PCR) was performed by using the Taq 2× Master Mix (Promega, Madison, Wis.) with ~100 ng leaf DNA as template. For the PCR identification of transgenic plants, primers GFP1 (5'-CTGAAGTTCATCTGCACCAC-3', SEQ ID NO:6) and GFP2 (5'-GGTGCTCAGGTAGTG-GTTGT-3' SEQ ID NO:7) were used to amplify the sequence of GFP. Template DNA was denatured at 94 for 2 min and 35 cycles of amplification was carried out as follows: 94° C. for 30 s, primer annealing at 52° C. for 30 s and extension at 72° C. for 1 min; The samples are followed by 7 min final extension at 72° C. PCR products were examined by electrophoresis through 1.0% agarose gels containing 1 µg mg·L$^{-1}$ ethidium bromide under UV illumination.

We have confirmed the transformation of guayule chloroplasts by PCR. We have positive PCR for the empty vector (control) lines, at least 4 lines, determined using the primers for GFP, as described above. We have guayule with the MEV6 cassette inserted and growing on selection.

The transformation frequency is about 5%. While this may seem a low frequency on its face, every other method yields 0%. (This finding is discussed further in Example 5 herein below)

Example 2

The following example illustrates an improved, highly efficient propagation and regeneration protocol for guayule transformation.

Materials and Methods

Plant Material

In vitro cultures of guayule were established from seeds of cultivar AZ-2 (ref) obtained from the USDA-ARS US-Arid Lands Research Center (Maricopa, Ariz.). Seeds were excised, then soaked sequentially in a 2% Tween-20 solution for 5 min, 70% ethanol for 1 min and in a 0.525% sodium hypochlorite (Clorox®) solution for 15 min. Seeds were triple rinsed with sterile water for 5 min each time. After germination, 3 cm of shoot tip was placed into a magenta box containing 88 mL of Murashige and Skoog (MS) (1962) basal medium supplemented with MS vitamins (PhytoTechnology Laboratories, Shawnee Mission, Kans.), 3% (w/v) sucrose and 0.3% (w/v) phatagel (Cat. No. p8169, Sigma). The solution was adjusted to pH 5.7-5.8 prior to autoclaving at 121° C. and 103.5 kPa (15 lb in$^{-2}$) for 30 min. This was the established medium used to maintain in vitro guayule cultures in our laboratory (Dong et al, 2006). The cultures were maintained in a growth chamber at 25° C. under a 16-h photoperiod provided by cool-white fluorescent lamps. The lamps provided a photosynthetic photon flux of 125 µmol·m$^{-2}$·s$^{-1}$, held at the top of the culture vessels. All of the stock cultures in the following experiment were maintained under these conditions.

The Effect of Basal Medium for Guayule Propagation

To evaluate the effect of basal medium salt on plant propagation, guayule shoots were cultured aseptically on either MS, woody plant medium (WPM) (Lloyd and McCown (1981) International Plant Propagator's Society, 30: 421-427 or Driver and Kuniyuki walnut (DKW) medium (Driver and Kuniyuki (1984) Hort. Sci 19:507). Vigorously growing 3-cm shoot tips were excised for guayule propagation (Table 1). All medium were supplemented with 0.1% MS vitamins, 3% (w/v) sucrose and 0.3% (w/v) phatagel (Sigma).

Efficiency of Guayule Shoots Regeneration

MS and DKW Medium with Cytokinin and Auxin Effects for Guayule Regeneration

All in vitro explants were aseptically grown on woody plant medium supplemented with 0.1% MS vitamins, 3% (w/v) sucrose and 0.3% (w/v) phatagel (Sigma). They were transferred to fresh medium (hormone free WPM) every 6-7 weeks as leaves were used as a source of explants for shoot regeneration.

Twenty shoot induction media, differencing in nutrient formulation (MS, DKW), were employed. The effect of naphthalene acetic acid (NAA) and 6-benzyladenine (BA) of guayule explants on shoot regeneration was examined in combinations of five levels of NAA (0.1, 0.25, 0.50, 0.75 and 1.0 mg·$L^{-1}$) and four levels of BA (0.25, 0.50, 0.75 and 1.0 mg·$L^{-1}$). Petri-dishes (100×20 mm) were cultured and kept under a 16 hour light period and 25° C. temperature. After 3 weeks the callus (explants) were transferred to fresh plates of the same media types and maintained for an additional 3 weeks. Data was collected at 3 and 6 week time intervals. The explants were evaluated for both shoot regeneration and callus growth.

Effect of Calcium Nitrate Tetrahydrate ($CaN_2O_6 4H_2O$) on DKW and MS Media for Regeneration To evaluate the effect of calcium nitrate on guayule regeneration, guayule explants were cultured on MS basal medium with plant growth regulators (PGRs) (1.0 mg·$L^{-1}$ BA and 0.1 mg·$L^{-1}$ NAA) and calcium nitrate. Six calcium nitrate concentrations, 0, 100, 250, 500, 750, 1000 and 1500 mg·$L^{-1}$, were tested (Table 3). Calcium nitrate was added to the culture medium before adjusting the pH to 5.7, prior to autoclaving. DKW basal medium (0.75 mg·$L^{-1}$ BA and 0.25 mg·$L^{-1}$ NAA) was used as a control.

Resistance of Regenerated Shoot on Media with Spectinomycin

To confirm whether the guayule explants were resistant to spectinomycin, leaf explants from control plants were cultured on regeneration DKW media that contained 0.75 mg·$L^{-1}$ BA and 0.125 mg·$L^{-1}$ NAA at various spectinomycin antibiotic levels. Several concentration of spectinomycin (0, 2, 4, 6, 8, 10, 12, 14, 16, 18 and 20 mg·$L^{-1}$) was added to the media to confirm the effects of antibiotic concentration on regeneration.

Experimental Design, Data Collection and Statistical Analysis

In the first experiments (the effects of basal medium for guayule propagation), 10 magenta boxes containing one shoot per magenta box were used for each treatment, and experiments were repeated three times. Plant performance was evaluated at 6 weeks for growing rate. The length of each plant was measured every 2 weeks for 6 weeks. The experimental design was a Completely Randomized Design (CRD), and the length date were evaluated by analysis of variance (ANOVA) using SAS version 9.1 (SAS Institute Inc. Cary, N.C.).

Results:

The Effect of Basal Medium for Guayule Propagation

Shoot tips grown on MS, DKW and WP medium were compared without the use of plant growth regulators. Results indicate that significantly faster rooting and significantly higher performance ratings were found for WPM than for the MS and DKW medium (Table 1). The lengths of shoots was also significantly higher when WPM was used.

TABLE 1

Effect of MS, DKW and WPM for guayule propagation after 4 weeks on three basal media

| Basal Medium | Day of first root coming | Performance rating[x] | Length of shoots (4 weeks) | Performance rating |
| --- | --- | --- | --- | --- |
| MS | 5.9 days | b | 4.22 cm | bc |
| DKW | 7.4 days | c | 3.87 cm | c |
| WPM | 4.8 days | a | 5.28 cm | a |

Mean length of guayule shoots grown on MS, DKW and WPM PGR-free phatagel medium after 4 weeks. Cultures were placed in growth chamber. The lamps provided a photosynthetic photon flux of 125 μmol · $m^{-2}$ · $s^{-1}$, held at the top of the culture vessels.
[x]The same letters in the different rows indicate that there is no significant difference (P ≤ 0.05)

Efficiency of Guayule Shoots Regeneration

MS and DKW Medium with BA and NAA Effects for Guayule Regeneration

Twenty combinations of NAA and BA concentrations were used for guayule regeneration. The maximum frequency of callus with multi shoots was obtained in the MS medium supplemented with 1.0 mg/L BA and 0.1 mg/L NAA (MS#4) and DKW medium supplemented with 0.75 mg·$L^{-1}$ BA and 0.25 mg·$L^{-1}$ NAA (DKW#7), respectively (Table 2). On those medium, each explant regenerated multiple shoots. The explants grown on MS medium showed larger size callus growing than DKW medium. Though there was no significant difference in shoot regeneration frequency between MS #4 and DKW #7. However, DKW #7 produced true shoots appeared from callus.

TABLE 2

Effect of cytokinin and auxin on MS and DKW media for regeneration of guayule

| | | | MS | | DKW | |
| --- | --- | --- | --- | --- | --- | --- |
| Condition # | BA (mg · $L^{-1}$) | NAA (mg · $L^{-1}$) | Callus/total explants | [x]Callus with multi shoots/total explants | Callus/total explants | [x]Callus with multi shoots/total explants |
| 1 | 0.25 | 0.10 | 16/30 | 12/30c | 20/30 | 7/30d |
| 2 | 0.50 | 0.10 | 25/30 | 18/30bc | 22/30 | 8/30cd |
| 3 | 0.75 | 0.10 | 29/30 | 24/30b | 30/30 | 22/30b |
| 4 | 1.00 | 0.10 | 30/30 | 30/30a | 30/30 | 22/30b |

TABLE 2-continued

Effect of cytokinin and auxin on MS and DKW media for regeneration of guayule

| Condition # | BA (mg · L$^{-1}$) | NAA (mg · L$^{-1}$) | MS Callus/total explants | MS $^x$Callus with multi shoots/total explants | DKW Callus/total explants | DKW $^x$Callus with multi shoots/total explants |
|---|---|---|---|---|---|---|
| 5  | 0.25 | 0.25 | 11/30 | 4/30e   | 11/30 | 3/30f  |
| 6  | 0.50 | 0.25 | 16/30 | 4/30e   | 18/30 | 11/30c |
| 7  | 0.75 | 0.25 | 25/30 | 19/30bc | 30/30 | 30/30a |
| 8  | 1.00 | 0.25 | 28/30 | 16/30c  | 29/30 | 24/30b |
| 9  | 0.25 | 0.50 | 9/30  | 0/30e   | 5/30  | 1/30e  |
| 10 | 0.50 | 0.50 | 12/30 | 6/30d   | 19/30 | 9/30cd |
| 11 | 0.75 | 0.50 | 19/30 | 12/30c  | 18/30 | 12/30c |
| 12 | 1.00 | 0.50 | 18/30 | 9/30c   | 20/30 | 13/30c |
| 13 | 0.25 | 0.75 | 4/30  | 0/30e   | 3/30  | 0/30f  |
| 14 | 0.50 | 0.75 | 9/30  | 2/30d   | 4/30  | 1/30e  |
| 15 | 0.75 | 0.75 | 17/30 | 6/30d   | 8/30  | 4/30e  |
| 16 | 1.00 | 0.75 | 22/30 | 8/30c   | 13/30 | 7/30d  |
| 17 | 0.25 | 1.00 | 0/30  | 0/30e   | 0/30  | 0/30f  |
| 18 | 0.50 | 1.00 | 2/30  | 0/30e   | 0/30  | 0/30f  |
| 19 | 0.75 | 1.00 | 9/30  | 2/30d   | 0/30  | 0/30f  |
| 20 | 1.00 | 1.00 | 8/30  | 2/30d   | 3/30  | 1/30e  |

Several concentrations of BA (0.25, 0.5, 0.75 and 1.0 mg · L$^{-1}$) and NAA (0.1, 0.25, 0.75 and 1 mg · L$^{-1}$) were added to MS or DKW medium to compare the effects of regeneration. For regeneration, three replicate plates were used, each with five 0.5 cm$^2$ leaf segments. Each experiment was repeated two times. Explants leaves were grown in petri-dish (20 × 100 mm) in sterile conditions at 25° C. and 16 h photoperiod. All media were supplemented with 0.1% MS vitamins, 3% (w/v) sucrose and 0.6% (w/v) phatagel (sigma). Explants were subcultured every two weeks and data were collect at six weeks.
$^x$The same letters in the different rows indicate that there is no significant difference (p ≤ 0.05)

Effect of Calcium Nitrate Tetrahydrate (CaN$_2$O$_6$4H$_2$O) on DKW and MS Media for Regeneration The addition of calcium nitrate tetrahydrate at moderate concentrations (0, 100, 250, 500 and 1000 mg·L$^{-1}$) into MS medium significantly improved the number of elongated shoots in both MS and DKW medium. Higher concentrations had a negative effect. (see e.g., Table 3).

TABLE 3

Effect of calcium nitrate tetrahydrate (CaN$_2$O$_6$4H$_2$O) on DKW and MS media for true shoots regeneration

| Calcium Nitrate | MS $^x$Size of Callus with multi shoots | MS $^y$Number of elongated shoots | DKW Size of Callus with multi shoots | DKW Number of elongated shoots |
|---|---|---|---|---|
| 0 mg · L$^{-1}$    | 4.8a  | 0/30  | 3.6a  | 4/30  |
| 100 mg · L$^{-1}$  | 4.5a  | 3/30  | 3.0b  | 6/30  |
| 250 mg · L$^{-1}$  | 4.4a  | 13/30 | 2.9b  | 3/30  |
| 500 mg · L$^{-1}$  | 4.1ab | 6/30  | 2.2bc | 0/30  |
| 1000 mg · L$^{-1}$ | 3.6c  | 0/30  | 2.0c  | 0/30  |
| 1500 mg · L$^{-1}$ | 2.1d  | 0/30  | 1.7d  | 0/30  |

Explants were grown on MS basal medium with 1.0 mg · L$^{-1}$ BA and 0.1 mg · L$^{-1}$ NAA or DKW basal medium with 0.75 mg · L$^{-1}$ BA and 0.25 mg · L$^{-1}$ NAA, and supplemented with either 0, 100, 250, 500, 750, 1000 or 1500 mg · L$^{-1}$ calcium nitrate tetrahydrate (CaN$_2$O$_6$4H$_2$O).
$^x$Callus were rated on a 5-point scale: (5) actively growing and callus size over 2 cm; (4) actively growing and callus size over 1.5 cm; (3) callus size over 1.0 cm; (2) callus size less than 1.0 cm; and (1) no callus
$^y$Total number of elongated true shoot from regenerated callus/total number of explants
The same letters in the different rows indicate that there is no significant difference (p ≤ 0.05).

TABLE 4

| Component | MS | MS (PhytoT.) | DKW | DKW (PhytoT.) | WPM |
|---|---|---|---|---|---|
| NH4NO$_3$           | 1650 | 1650  | 1416 | 1416   | 400  |
| KNO$_3$             | 1900 | 1900  | —    | —      | —    |
| Ca(NO$_3$)2•4H2O    | —    | —     | 1968 | 1367   | 556  |
| CaCl$_2$•2H$_2$O    | 440  | 332.2 | 149  | 112.5  | 96   |
| K$_2$SO$_4$         | —    | —     | 1559 | 1559   | 990  |
| MgSO$_4$•7H$_2$O    | 370  | 180.7 | 740  | 361.5  | 370  |
| (NH$_4$)$_2$SO4     | —    | —     | —    | —      | —    |
| MnS0$_4$•H$_2$O     | —    | —     | —    | —      | —    |
| NaH$_2$PO$_4$       | —    | —     | —    | —      | —    |
| KH$_2$PO$_4$        | 170  | 170   | 265  | 265    | 170  |
| MnSO$_4$•4H$_2$O    | 22.3 | 16.9  | 33.5 | 33.5   | 22.3 |
| Na$_2$MoO$_4$•2H$_2$O | 0.25 | 0.25 | 0.39 | 0.39  | 0.25 |
| ZnSO$_4$•7H$_2$O    | 8.6  | 8.6   | —    | —      | 8.6  |
| Zn(NO$_3$)$_2$•6H$_2$O | — | —     | 17   | 17     | —    |

TABLE 4-continued

| Component | MS | MS (PhytoT.) | DKW | DKW (PhytoT.) | WPM |
|---|---|---|---|---|---|
| KI | 0.83 | 0.83 | — | — | — |
| $H_3BO_3$ | 6.2 | 6.2 | 4.8 | 4.8 | 6.2 |
| $CuSO_4 \cdot 5H_2O$ | 0.025 | 0.25 | 0.25 | 0.25 | 0.25 |
| $COCl \cdot 6H_2O$ | 0.025 | 0.25 | — | — | — |
| $NiSO_4 \cdot 6H_2O$ | — | — | 0.005 | — | — |
| $FeSO_4 \cdot 7H_2O$ | 27.8 | 27.8 | 33.8 | 33.8 | 27.8 |
| $Na_2EDTA \cdot 2H_2O$ | 37.3 | 37.3 | 45.4 | 45.4 | 37.3 |
| Myo-inositol | 100 | 100 | 100 | 100 | 100 |
| Thiamin-HCL | 0.1 | 0.1 | 2 | 2 | 1 |
| Nicotinic acid | 0.5 | 0.5 | 1 | 1 | 0.5 |
| Pyridoxine-HCL | 0.5 | 0.5 | — | — | 0.5 |
| Glycine | 2 | 2 | 2 | 2 | 2 |
| Glutamine | — | — | — | — | 2 |

Resistance of Regenerated Shoot on Media with Spectinomycin

Spectinomycin present in the media had a significant effect on callus formation and shoot regeneration of guayule. Callus formation and shoot emergence was not affected by spectinomycin at 8 mg·$L^{-1}$, but was significantly reduced at 10 mg·$L^{-1}$ and completely inhibited by 12 mg·$L^{-1}$ or higher.

Example 3

The following example illustrates transformation of guayule using the following standard bombardment protocol.

Chloroplast Transformation with Guayule Chloroplast Specific Vector:

The leaves of *Parthenium argentatum* (guayule) of AZ-2 lines was transformed using S550d Gold Carrier Particles (SeaShell Technology, CA, USA). A modified protocol for bombarding five leaf samples is described as following. Sonication of S550d particles at 40 kHz (Ultrasonic Cleaner Branson, Calif., USA). Transfer 50-µl to 1.5 mL microcentrifuge tube. Add 20-µl plasmid (0.5-1.0-µg/ul) to S550d particles and vortex the mixture briefly. Add 70-µl Precipitation Buffer (supplied by vendor) and vortex briefly. Incubate 3 min at room temp. Spin tube at 10,000 rpm for 10 sec. Wash pellet with 500 ul cold Abs EtOH. Vortex briefly, spin at 10,000 rpm for 10 sec. Discard supernatant and resuspend the precipitated DNA and S550d particles in 50 µl absolute Alcohol. After brief sonication, distribute 10-µl mixture per microcarrier disc. DNA coated particles were bombarded over leaf disks using Biolistic® PDS-1000/He (Bio-rad), at 1100 psi rupture disc pressure and 9 cm distance and transgenic shoots were selected on 100 mg/L spectinomycin, following the tissue culture method as described by Dong et al. (2006) Plant Cell Rep., 25 (2006), pp. 26-34.

No transformants were recovered. See Example 5 hereinbelow.

Example 4

The following example illustrates transformation of guayule using the following standard protoplast method.

Transformation of guayule using a protoplast method, as described by Pan et al. (2004), Kofer et al. (1998) and Golds et al. (1993) was attempted. See Pan, Z G.; Liu, C Z.; Zobayed, S M A.; Saxena, P K. (2004) Plant regeneration from mesophyll protoplasts of *Echinacea purpurea*. Plant cell, tissue and organ culture. 77: 251-255; Kofer, W., Eibl, C., Steinmueller, K., and Koop, H-U. (1998) PEG-mediated plastid transformation in higher plants. In Vitro Cell. Dev. Biol. Plant. 34:303-309; Golds, T., Maliga, P. and Koop H-U. (1993) Stable Plastid Transformation in PEG-treated Protoplasts of *Nicotiana tabacum*. Nature Biotechnology 11: 95-97.

Transient expression of GFP into transformed Guayule chloroplasts was observed under a fluoroscent microscope in micro calli of a transformed protoplast, after 1 week of culture on Semi-solid MS medium, as shown in following picture. Unfortunately, no plants could be recovered from the transformed protoplasts.

Example 5

The following example provides a summary Table comparing transformation efficiencies for guayule transformed according to the methods disclosed herein (Example 1 and Example 2, hereinafter "our method") and the standard methods described in Examples 3 and 4.

TABLE 5

|  | Example 3 | Example 4 | Our method |
|---|---|---|---|
| # attempts | 630 | 20 | 450 |
| # transformed plants recovered | 0 | 0 | 33 |
| % efficiency | 0% | 0% | 7.3% |

Example 6

The following Example illustrates chloroplast transformation of guayule (*Parthenium argentatum*) using an optimized protocol.
Preparation of Plasmid DNA The pUY-Gua-MEV6 (FIG. 1) and pUY-Gua-aadA/ NPTII/GFP chloroplast transformation plasmids were used in this example. Both plasmids feature guayule-specific flanking sequences to target insertion into the guayule chloroplast. The flanking sequences were identified by analysis of the chloroplast genome of guayule (Kumar et al. 2009 *BMC Plant Biology.* 9:131) by PCR. Based on the genome, primers were designed to target the flanking sequences and were PCR amplified, cloned, and inserted into the plasmids. The pUY-Gua-MEV6 plasmid contained the 6-gene cluster comprising the complete yeast mevalonate pathway. pUY-Gua-aadA/NPTII/GFP chloroplast plasmid contained aadA, NPTII and gfp genes. The aadA gene, included in the operon, confers resistance to spectinomycin, the NPTII gene, included in the operon, confers resistance to kanamycin, and plant tissues with the GFP gene exhibit fluorescence from Green Fluorescent Protein when exposed to visible light at 509 nm.

The guayule chloroplast transformation vector was constructed following that previously described (Kumar and Daniell, 2004 *Methods Mol. Biol.* 267, 365-383). Flanking sequences for homologous recombination were amplified using the Guayule Chloroplast Genome Sequences (Kumar et al., 2009, supra) with the forward primer GuaFL_F: GGCCGACACTGACACTGAGAGACGA (SEQ ID NO:8) and the reverse primer GuaFL_R: GCCATCCTAAGGT-GCTGCTAAATGGA (SEQ ID NO:9). The 3.0 kb PCR product was amplified using PFU-Ultra Fidelity Polymerase (Stratagene) following vendor's instructions. The PCR product was purified and sequenced. The complete DNA sequence of flanking region, which is 100% specific for chloroplast transformation of *Parthenium argentatum* (Guayule) line AZ-2, is given as below:

```
Guayule Flanking Cp-DNA sequence
                                    (SEQ ID NO: 10)
GGCCGACACTGACACTGAGAGACGAAAGCTAGGGGAGCGAATGGGATTAG

ATACCCCAGTAGTCCTAGCCGTAAACGATGGATACTAGGCGCTGTGCGTA

TCGACCCGTGCAGTGCTGTAGCTAACGCGTTAAGTATCCCGCCTGGGGAG

TACGTTCGCAAGAATGAAACTCAAAGGAATTGACGGGGGCCCGCACAAGC

GGTGGAGCATGTGGTTTAATTCGATGCAAAGCGAAGAACCTTACCAGGGC

TTGACATGCCGCGAATCCTCTTGAAAGAGAGGGGTGCCTTCGGGAACGCG

GACACAGGTGGTGCATGGCTGTCGTCAGCTCGTGCCGTAAGGTGTTGGGT

TAAGTCCCGCAACGAGCGCAACCCTCGTGTTTAGTTGCCATCATTGAGTT

TGGAACCCTGAACAGACTGCCGGTGATAAGCCGGAGGAAGGTGAGGATGA

CGTCAAGTCATCATGCCCCTTATGCCCTGGGCGACACACGTGCTACAATG

GCCGGGACAAAGGGTCGCGATCCCGCGAGGGTGAGCTAACTCCAAAAACC

CGTCCTCAGTTCGGATTGCAGGCTGCAACTCGCCTGCATGAAGCCGGAAT

CGCTAGTAATCGCCGGTCAGCCATACGGCGGTGAATCCGTTCCCGGGCCT

TGTACACACCGCCCGTCACACTATGGGAGCTGGCCATGCCCGAAGTCGTT

ACCTTAACCGCAAGGAGGGGGATGCCGAAGGCAGGGCTAGTGACTGGAGT

GAAGTCGTAACAAGGTAGCCGTACTGGAAGGTGCGGCTGGATCACCTCCT

TTTCAGGGAGAGCTAATGCTTGTTGGGTATTTTGGTTTAACACTGCTTCA

CACCCAAAAAGAAGGGAGCTACGTCTGAGTGAAACTTGGAGATGGAAGTC

TTCTTTCGTTTCTCGACAGTGAAGTAAGACCAAGCTCATGAGCTTATTAT

CTCAGGTCGGAACAAGTTGATAGGATCCCCCTTTTTACGTCCCCATGCCG

CCTGTGTGGTGACATGGGCCGAAAAAAGGAAAGAGAGGGATGGGGTTTCT

CTCGCTTTTGGCATAGTGGGCCCCCGGTGGGGGGCTCGCACGACGGGCTA

TTAGCTCAGTGGTAGAGCGCGCCCCTGATAATTGCGTCGTTGTGCCTGGG

CTGTGAGGGCTCTCAGCCACATGGATAGTTCAATGTGCTCATCGGCGCCT

GACCCTGAGATGTGGATCATCCAAGGCACATTAGCATGGCGTACTCCTCC

TGTTCGAACCGGGGTTTGAAACCAAACTTCTCCTCAGGAGGATAGATGGG

GCGATTCAGGTGAGATCCAATGTAGATCCAACTTTCGATTCACTCGTGGG

ATCCGGGCGGTCCGGGGGGACCACCATGGCTCCTCTCTTCTCGAGAATC

CATACATCCCTTATCAGTGTATGGACAGCTATCTCTCGAGCACAGGTTTA

GGTTCGGCCTCAATGGGAAAATAAAATGGAGCACCTAACAACGCATCTTC

ACAGACCAAGAACTACGAGATCACCCCTTTCATTCTGGGGTGACGGAGGG

ATCATACCATTCGAGCCTTTTTTTTTCATGCTTTTCCCCGAGGTCTGGAG

AAAGCTGAAATCAAATGGGATGTGTCTATTTATCTATCTCTTGACTCGAA

ATGGGAGCAGGTTTGAAAAAGGATCTTAGAGTGTCTAGGGTTGGGCCAGG

AGGGTCTCTTAACGCCTTCTTTTTTCTTCTCATCGGAGTTCTTTCACAAA

GACTTGCCATGGTAAGGAAGAAGGGGGAACAGGCACACTTGGAGAGCGC

AGTACAACGGAGAGTTGTATGCTGCGTTCGGGAAGGATGAATCGCTCCCG

AGAAAGGAATCTATTGATTCTCTCCCAATTGGTTGGACCGTAGGTGCGAT

GATTTACTTCACGGGCGAGGTCTCTGGTTCAAGTCCAGGATGGCCCAGCT

GCGCCAGGGAAAAGAATAGAAGAAGCATCTGACTACTTCATGCATGCTCC

ACTTGGCTCGGGGGGATATAGCTCAGTTGGTAGAGCTCCGCTCTTGCAAT

TGGGTCGTTGCGATTACGGGTTGGATGTCTAATTgtCCAGGCGGTAATGA

TAGTATCTTGTACCTGAACCGGTGGCTCACTTTTTCTAAGTAATGGGGAA

GAGGACCGAAACATGCCACTGAAAGACTCTACTGAGACAAAGATGGGCTG

TCAAGAACGTCAAGAACGTAGAGGAGGTAGGATGGGCAGTTGGTCAGATC

TAGTATGGATCGTACATGGACGGTAGTTGGAGTCGGCGGCTCTCCTAGGG

TTCCCTTATCGGGGATCCCTGGGGAAGAGGATCAAGTTGGCCCTTGCGAA

CAGCTTGATGCACTATCTCCCTTCAACCCTTTGAGCGAAATACGGCAAAA

GGAAGGAAAATCCATGGACCGACCCCATCATCTCCACCCCGTAGGAACTA

CGAGATTACCCCAAGGACGCCTTCGGCATCCAGGGGTCACGGACCGACCA

TAGAACCCTGTTCAATAAGTGGAACGCATTAGCTGTCCGCTCTCAGGTTG

GGCAGTAAGGGTCGGAGAAGGGCAATCACTCATTCTTAAAACCAGCGTTC

TTAAGGCCAAAGAGTCGGCGGAAAAGGGGGAAAGCTCTCCGTTCCTGGT

TCTCCTGTAGCTGGATCCTCCGGAACCACAAGAATCCTTAGTTAGAATTA

GAATGCGATTCCAACTCAGCACCTTTTGAGTTAGATTTTGAGAAGAGTTG

CTCTTTGGAGAGCACAGTACGATGAAAGTTGTAAGCTGTGTTCGGGGGGG

AGTTATTGTCTATCGTTGGCCTCTATGGTAGAATCAGTCGGGGGACCTGA

GAGGCGGTGGTTTACCCTGCGGCGGATGTCAGCGGTTCGAGTCCGCTTAT

CTCCAACTCGTGAACTTAGCCGATACAAAGCTATATGATAGCACCCAATT

TTTCCGATTCGGCGGTTCGATCTATGATTTATCATTCATGGACGTTGATA

AGATCCATCCATTTAGCAGCACCTTAGGATGGC
```

To construct the Guayule specific chloroplast transformation vector, the above rrn16-trnI-trnA region (Flanking DNA sequence) was inserted into the easily available pUC19 cloning vector, which has one ampicillin resistance gene.

The pUC19 vector was digested with PvuII and SspI and the blunt PCR fragment of flanking sequence was directlycloned into pUC19 vector following standard molecular techniques. The other essential elements like Prrn promoter (Silhavy and Maliga, (1998) Current Genetics 34:67-70) and regulatory sequences were amplified using oligos as described from the tobacco chloroplast genome (see e.g., Kumar, S. & Daniell, H. Methods Mol. Biol. 267, 365-383 (2004)).

Figure 4:
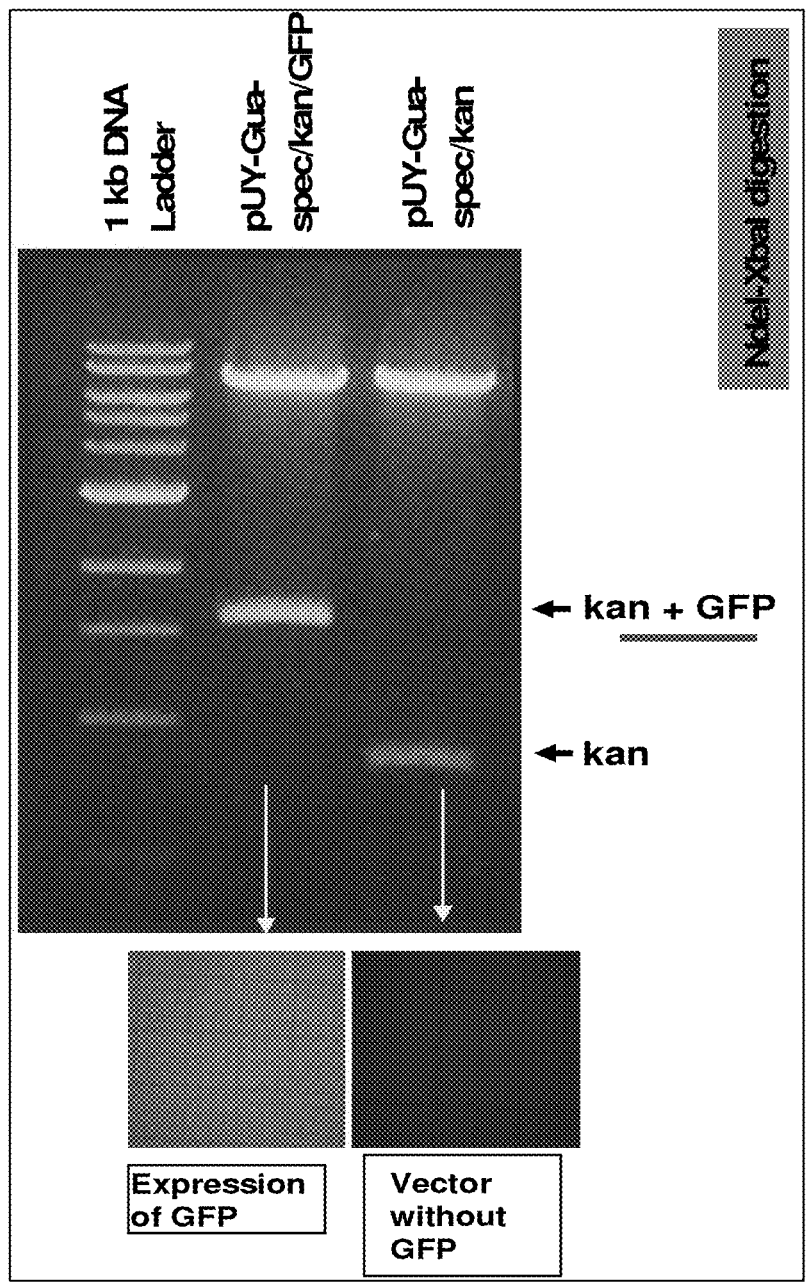
FIG. 4. The vector pUY-Gua-aadA/nptII/GFP (aka pUY-Gua-spec/kan/GFP) was tested with Nde1-XbaI digestion. The small bands in the middle lane and the right lane showed different sizes, representing NPTII gene plus GFP gene or NPTII gene analog. A GFP fluorescence was observed in the E. coli cells under a fluorescent microscope as shown below the gel image, illustrating the functionality of the GFP gene in this construct.

The psbA (light regulated) promoter along with 5' UTR was obtained as synthetic DNA from Bio Basic Inc. (Canada). The empty vector control pUY-Gua-aadA/nptII/GFP was made for optimization of Guayule's chloroplasts transformation. The physical map of pUY-Gua-aadA/nptII/GFP is given below and the vector was tested with Nde1-XbaI digestion and GFP fluorescence was observed in the *E. coli* cells under fluorescent microscope as shown in FIG. 4.

Plant Transformation

The guayule plants were grown aseptically on hormone free Wood Plant Media (WPM) supplemented with 0.3% (w/v) gelrite, 3.0% (w/v) sucrose and 2.0% (w/v) activated Charcoal (Sigma). All media were adjusted to a pH of 5.7-5.8 prior to autoclaving at 121° C. and 103.5 kPa (15 lb in-2) for 20 min. All of the stock cultures in the following experiments were maintained under these conditions.

pUY-Gua-MEV6 and pUY-Gua-aadA/NPTII/GFP plasmid DNAs (12.5 μg each) were transformed in guayule using standard micro-projectile bombardment procedures as described by Blechl and Anderson (1996) Nat. Biotechnol. 14:875-879. Guayule leaves harvested from in vitro-grown guayule plants were cut into 0.5 cm² segments. The explants were placed in MS supplemented with 5 mg·L$^{-1}$ trans-zeatin-riboside for bombardment and recovery. Leaves were bombarded with the PDS 1000/He Biolistic Gun (Bio-Rad) at 1100 psi. In each bombardment, 2.1 mg of 0.6 μm gold particles and 12.5 μg of plasmid DNA were used.

The bombarded guayule leaves were incubated in the MS supplemented with 5 mg·L$^{-1}$ trans-zeatin-riboside for recovery. After 5 days of recovering, the explants were transferred onto Callus and Shoot Induction Medium for selection of resistant shoots [MS medium supplemented with 1.0 mg·L$^{-1}$ BA, 0.1 mg·L$^{-1}$ NAA and 250 mg·L$^{-1}$ calcium nitrate]; 12 mg·L$^{-1}$ spectinomycin was used for selecting transformed cells. After 4 weeks, induced calli and small shoot were transferred to Shoot Induction Medium [DKW supplemented with 0.75 mg·L$^{-1}$ BA and 0.25 mg·L$^{-1}$ NAA and 250 mg·L$^{-1}$ calcium nitrate]; 15 to 20 mg·L$^{-1}$ spectinomycin was used for selecting transformed shoots. Every 2 weeks regenerated shoots were subcultured until shoots were elongated. Elongated shoots were transferred to Rooting Medium [WPM supplemented with 10 m·L$^{-1}$ spectinomycin]. The shoots were later transplanted to soil after confirmation by PCR.

Plant Genomic DNA Isolation and PCR Analysis

To confirm the presence of the transgene in plants that were spectinomycin-resistant, guayule genomic DNA was isolated from 0.5 g transgenic and non-transgenic plant leaf tissues using a GeneElute™ Plant Genomic DNA Miniprep Kit (Sigma, USA) according to the manufacturer's protocol. 50 ng genomic DNA was used for PCR amplification by using the spectinomycin-gfp gene primers (forward 5'-TGA ATG AAC TGC AGG ACG AG-3' (SEQ ID NO:11) primers and reverse 5'-GGG TGT TCT GCT GGT AGT GG-3' (SEQ ID NO:12)). The expected size for the gene was 1200 bp. Amplified fragments were separated on 1% agarose gels using a DNA 1 KB ladder (Fisher Scientific Inc., Pittsburgh, Pa.).

Results

Figure 5:
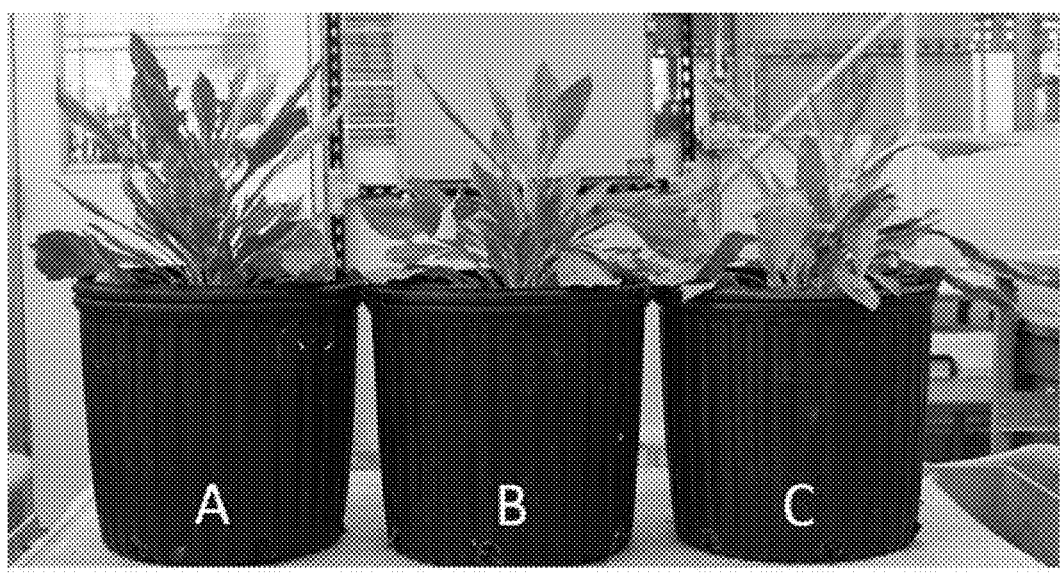
FIG. 5. Greenhouse guayule plants (A) non-transgenic control plant (B) pUY-Gua-aadA/NPTII/GFP transgenic plant (C) pUY-Gua-MEV6 transgenic plant. The figure illustrates that there were no significant differences among 9-week-old transgenic and non-transgenic plants in plant height and shape of plants.
Figure 6A:
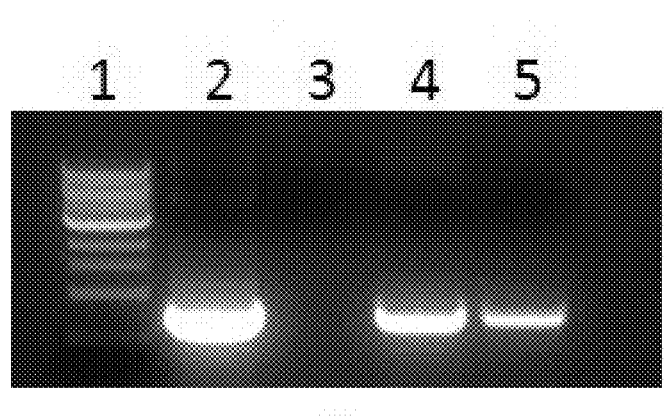
FIG. 6. A: PCR amplification with HMGS gene primers (forward 5'-TTGGACTTCCCGGACATTAG-3', SEQ ID NO:2 primers and reverse 5'-TTTCTCGGTGACCAACA-CAC-3', SEQ ID NO:3). Lane 1: 1 Kb marker, lane 2: plasmid DNA, lane 3: non-transgenic control plant, lanes 4 and 5 pUY-Gua-MEV6 transgenic plants (0.7 bp).
Figure 6B:
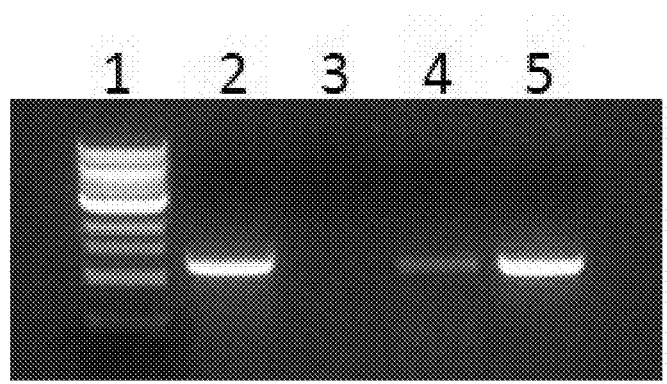

Guayule plants transformed by pUY-Gua-MEV6 and pUY-Gua-aadA/NPTII/GFP genes and non-transgenic control plants were transferred into soil after confirmation by PCR. Plants were moved to the greenhouse; all grew normally and all transgenic plants appeared morphologically normal. There were no significant differences among 9-week-old transgenic and non-transgenic plants in plant height and shape of plants (FIG. 5).

Both pUY-Gua-MEV6 (FIG. 1 and FIG. 2) and pUY-Gua-aadA/NPTII/GFP genes were PCR amplified using specific HMGS primer pairs (forward 5'-TTGGACTTCCCGGA-CATTAG-3' (SEQ ID NO:2) primers and reverse 5'-TTTCTCGGTGACCAACACAC-3' SEQ ID NO:3) and aadA-GFP gene primers pairs (forward 5'-TGAATGAACT-GCAGGACGAG-3' (SEQ ID NO:4) primers and reverse 5'-GGGTGTTCTGCTGGTAGTGG-3', SEQ ID NO:5), yielding the expected band sizes of 0.7 kb and 1.2 kb, respectively.

The efficiency of chloroplast transformation using this method was calculated using two criteria. First was based on plants confirmed positive by PCR after surviving selection media [DKW with 15 to 20 mg·L$^{-1}$ spectionmycin]. In that case, the 6.9% of guayule plants (8 total) transformed by the pUY-Gua-MEV6 and 13.0% of guayule plants (9 total) transformed by the pUY-Gua-aadA/NPTII/GFP gene were confirmed transplastomic. The second basis used was that of the number of PCR-confirmed transplastomic plants out of all attempted bombardment experiments. In that case, 699 guayule explants were used for pUY-Gua-MEV6 transformation resulting in a 1.14% transformation efficiency and 523 explants were used for pUY-Gua-aadA/NPTII/GFP, resulting in a 1.72% transformation efficiency (Table 6).

TABLE 6

Efficiency of chloroplast transformation of guayule

| Plasmid | Number of bombarded Explants | Number of Resistance on selection media | Number of PCR positive | % of PCR positive[a] | % of final efficiency[b] |
|---|---|---|---|---|---|
| pUY-MEV6 | 699 | 116 | 8 | 6.9 | 1.14 |
| pUY-Gua-aadA/nptII/GFP | 523 | 69 | 9 | 13.0 | 1.72 |

[a] % of PCR positive = (Number of PCR positive/Number of spectinomycin resistance on selection media) × 100
[b] % of final efficiency = (Number of PCR positive/Total number of Explants) × 100

Example 7

The following Example summarizes compositions and methods disclosed herein.

| Chloroplast transformation of guayule | | | |
|---|---|---|---|
| | | Methods and Materials | Kang et al. |
| Plant material | | | Guayule (*Parthenium argentatum* Gray) Leaf segment |
| Media | Propagation media | | WPM w/activated charcoal |
| | | Activated charcoal for propagation media | 1-10 g/L, or 1-5 g/L, or 2 g/L |
| | Selection media | Callus induction | MS or DKW w/CaNO3 |
| | | Shoot elongation | MS or DKW w/CaNO3 |
| | | Addition supplement on media- Calcium nitrate tetrahydrate | 50-1500 mg/L, or 250 mg/L |
| | Rooting media | | WPM |
| Dipping method for Rooting | | Hormone concentration and period time | 1-10 mg/ml IBA 1-10 min, or 2 mg/ml for 2 min 1-10 mg/ml IAA for 1-10 min 1-10 mg/ml NAA for 1-10 min |
| Zeatin shock (3 hours before and immediately after introducing the transgene for 5 days) | Trans zeatin riboside | | 1-160 mg/L, or 5 mg/L |
| | Trans zeatin | | 1-160 mg/L |
| | Cis-zeatin | | 1-160 mg/L |
| | Dihydrozeatin | | 1-160 mg/L |
| | N6 adenine (lp) | | 1-160 mg/L |
| Recovery, following transgene introduction and zeatin shock | | Period of time without selection | 1-10 days, or 1-7 days, or 5 days |
| | | Under light, move to selection | Days to weeks |

Abbreviations:
WPM: woody plant medium
MS: Murashige and Skoog medium
DKW: Driver and Kuniyuki walnut medium
IBA: Indole-3-butyric acid
BA: $N_5$-benzylaminopurine
NAA: α-naphthaleneacetic acid
IPT: adenosine phosphate-isopentenyl-transferase Example 7

The following Example illustrates that growing on medium supplemented with activated charcoal results in plants having increased chlorophyll content.
Chlorophyll Content Analysis by Minolta Chlorophyll Meter SPAD-502

Plants grown in the medium supplemented with activated charcoal (AC) were significantly healthier and greener in color than those grown in media without AC. Therefore, leaves were analyzed for chlorophyll content. Four leaves from each of the in vitro treatments were sampled. We also analyzed the chlorophyll content of plants grown on potting mix without AC in a greenhouse. Soil plant analysis development (SPAD) Chlorophyll meter were taken at the center of the leaves throughout the experiments.

Results

Guayule grown on basal wood plant medium (WPM) with AC appeared to have greener leaves. Guayule leaves from shoots grown on the medium containing AC had 44.4-46.4 μmol photons $m^{-2}$ SPAD value, much higher than those grown on the without AC (26.3 μmol photons $m^{-2}$). The greenhouse plants grown under the sun light had 52.5-54.5 μmol photons $m^{-2}$. pUY-MEV6 transgenic plant showed 30.5 μmol photons $m^{-2}$ SPAD value.

| | Chlorophyll content analysis by Minolta chlorophyll meter SPAD-502 | | | | | |
|---|---|---|---|---|---|---|
| | Growth chamber WPM without AC | Greenhouse #1 Plant grown on Potting mix | Greenhouse #2 Plant grown on Potting mix | Growth chamber #1 WPM with AC[a] | Growth chamber #2 WPM with AC[a] | Growth chamber pUY-MEV6 transgenic plant with AC[a] |
| SPAD value[b] (μmol photons $m^{-2}$) | 26.3 | 54.5 | 52.6 | 46.4 | 44.4 | 30.5 |

Plants were grown on plant growth regulator free WPM basal medium, solidified with gelrite, and supplemented with 2 g · $L^{-1}$ activated charcoal (AC). The greenhouse plants were grown on potting mix soil with AC.
[a]AC: 2g/L activated charcoal
[b]SPAD value: For each treatment, the average of 3 measurements was given as SPAD value It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for transforming guayule chloroplasts to provide a transplastomic guayule plant, the method comprising:

(i) growing guayule plants on hormone free media supplemented with activated charcoal to provide cultured guayule plants;

(ii) collecting leaves from the cultured guayule plants to provide leaves from the cultured guayule plants;

(iii) placing the leaves from the cultured guayule plants in medium comprising trans-zeatin-riboside for bombarding and recovery;

(iv) bombarding the leaves from the cultured guayule plants with gold particles, wherein the gold particles are coated with chloroplast transformation vector, thereby providing bombarded guayule leaves, and wherein the chloroplast transformation vector comprises guayule specific flanking sequences and a transgene cassette, wherein said guayule specific flanking sequences are 5' and 3' to said transgene cassette, wherein said guayule specific flanking sequences target insertion of the chloroplast transformation to chloroplast DNA, and wherein said transgene cassette comprises a transgene and a heterologous selectable marker gene;

(v) incubating the bombarded guayule leaves in the medium comprising trans-zeatin-riboside, to provide recovered bombarded guayule leaves;

(vi) transferring the recovered bombarded guayule leaves to Callus and Shoot Induction medium comprising a selection agent and between about 100 mg/L to about 450 mg/L calcium nitrate;

(vii) growing the recovered bombarded guayule leaves in Callus and Shoot Induction medium to provide calli and small shoots;

(viii) transferring the calli and small shoots to Shoot Induction Medium wherein the Shoot Induction Medium comprises between about 100 mg/L to about 450 mg/L calcium nitrate;

(ix) growing the calli and small shoots in the Shoot Induction Medium until shoots are elongated, to provide elongated shoots;

(x) transferring the elongated shoots to Rooting Medium comprising a selection agent;

(xi) growing the elongated shoots on the Rooting Medium until roots are formed, to provide rooted shoots;

(xii) transplanting the rooted shoot to soil, and (xiii) growing the rooted shoots in the soil;

thereby providing a transplastomic guayule plant.

2. The method of claim 1, wherein said transgene comprises nucleotides 4657 through 12820 of SEQ ID NO: 1.

3. The method of claim 1, wherein said transgene is 5' to said heterologous selectable marker gene.

4. The method of claim 1, wherein said heterologous selectable marker gene is 5' to said transgene.

5. The method of claim 1, wherein said guayule specific flanking sequences that are 5' to said transgene cassette are nucleotides 1874-3821 of SEQ ID NO: 1, and wherein said guayule specific flanking sequences that are 3' to said transgene cassette are nucleotides 14991-16075 of SEQ ID NO: 1.

* * * * *